(12) United States Patent
Peacock

(10) Patent No.: US 9,862,821 B2
(45) Date of Patent: Jan. 9, 2018

(54) HYDROLYSIS RESISTANT COMPOSITIONS

(71) Applicant: E I DU PONT DE NEMOURS AND COMPANY, Wilmington, DE (US)

(72) Inventor: Judith Alison Peacock, Vaud (CH)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 440 days.

(21) Appl. No.: 14/281,972

(22) PCT Filed: Mar. 12, 2013

(86) PCT No.: PCT/US2013/030317
§ 371 (c)(1),
(2) Date: May 20, 2014

(87) PCT Pub. No.: WO2014/035472
PCT Pub. Date: Mar. 6, 2014

(65) Prior Publication Data
US 2014/0275346 A1    Sep. 18, 2014

Related U.S. Application Data

(60) Provisional application No. 61/696,016, filed on Aug. 31, 2012.

(51) Int. Cl.
| | | |
|---|---|---|
| C08K 3/32 | (2006.01) | |
| C08K 3/34 | (2006.01) | |
| C08K 3/40 | (2006.01) | |
| C08K 5/49 | (2006.01) | |
| C08K 7/00 | (2006.01) | |
| C08L 63/00 | (2006.01) | |
| C08L 67/00 | (2006.01) | |
| C08L 67/02 | (2006.01) | |
| C07F 9/12 | (2006.01) | |
| C07F 9/30 | (2006.01) | |
| C08K 5/523 | (2006.01) | |

(52) U.S. Cl.
CPC .............. C08L 67/02 (2013.01); C07F 9/12 (2013.01); C07F 9/301 (2013.01); C08K 3/32 (2013.01); C08K 5/523 (2013.01); C08K 2003/325 (2013.01)

(58) Field of Classification Search
CPC ..... C08K 2003/325; C08K 3/32; C08L 67/00; C08L 67/02; C08L 63/00–63/10; C09D 167/00; C09D 167/02; C09D 163/00–163/10; C09J 167/00; C09J 167/02; C09J 163/00–163/10
See application file for complete search history.

(56) References Cited

U.S. PATENT DOCUMENTS

| | | | |
|---|---|---|---|
| 3,919,383 A | 11/1975 | Yankowsky | |
| 4,456,723 A | 6/1984 | Breitenfellner et al. | |
| 5,638,003 A * | 6/1997 | Hall | G01R 31/1263 324/514 |
| 6,048,626 A | 4/2000 | Tsuzuki et al. | |
| 6,248,814 B1 * | 6/2001 | Hironaka | C08K 3/0008 524/405 |
| 6,838,529 B2 | 1/2005 | Kumazawa et al. | |
| 6,974,846 B2 | 12/2005 | Garrison et al. | |
| 7,008,983 B2 | 3/2006 | Garrizon et al. | |
| 7,893,141 B2 | 2/2011 | Wit et al. | |
| 2010/0204406 A1 * | 8/2010 | Suzuki | B32B 27/32 525/221 |

FOREIGN PATENT DOCUMENTS

WO    2006039299    4/2006

OTHER PUBLICATIONS

M. M J.Friday, "A Comparison of Tension Test data Using ASTM D 638 and ISO 527," Limitations of Test Methods for Plastics, ASTM STP 1369, Am. Soc. for Testing and Materials, pp. 35-43 (2000).*
Alpha and Omega Semiconducor, Power Semiconductor Reliability Handbook (2010).*
Ellis et al., Polymers: A Property Database, 2nd ed. (2009).*
International Search Report in International Application PCT/US13/30317, from which this national stage application claims priority as a 35 USC 371 filing.
Svensk Standard SS-EN ISO527-2:2012, "Plastics—Determination of tensile properties—Part 2: Test conditions for moulding and extrusion plastics", Swedish Standards Institute, Mar. 14, 2012.
Svensk Standard SS-EN IS0527-1:2012, "Plastics—Determination of tensile properties—Part 1: General principles", Swedish Standards Institute, Mar. 3, 2012.
International Standard ISO527-2, "Plastics—Determination of tensile properties—Part 2: Test conditions for moulding and extrusion plastics", First Edition, Jun. 15, 1993.
International Standard ISO527-1, "Plastics—Determination of tensile properties—Part 1: General principles", First Edition, Jun. 15, 1993.
International Standard ISO527-1, "Plastics—Determination of tensile properties—Part 1: General principles, Amendment 1: Details of extensometer", First Edition, Jun. 15, 1993, Amendment 1, Sep. 1, 2005.
International Standard ISO11443, "Plastics—Determination of the fluidity of plastics using capillary and slit-die rheometers", Second Edition, Mar. 1, 2001.

* cited by examiner

Primary Examiner — Kregg T Brooks

(57) ABSTRACT

Polyester compositions comprising: a) at least one semi-aromatic polyester resin; b) at least one reinforcing agent; c) hydroxyapatite; d) at least one epoxy component having two or more epoxy functional groups per molecule of the epoxy component; and optionally, at least one toughener, wherein the compositions exhibit the combined property of a desirable melt viscosity stability and a desirable hydrolysis resistance to articles molded from the compositions. Articles molded or extruded from these compositions especially, electric and electronic components. Methods of maintaining melt viscosity stability of a melt-mixed composition while simultaneously retaining tensile strength in the article prepared from the melt-mixed composition.

20 Claims, No Drawings

HYDROLYSIS RESISTANT COMPOSITIONS

CROSS-REFERENCE TO RELATED APPLICATIONS

This application claims priority under 35 U.S.C. 365(c) from International Application No. PCT/US13/30317, filed 12 Mar. 2013, currently pending, which claims priority under 35 U.S.C. 1.19(e) from U.S. Prov. Pat. App. No. 61/696,016, both of which applications are hereby incorporated herein by reference.

OVERVIEW

Disclosed herein are polyester compositions having an epoxy functionality and hydroxy apatite and exhibiting improved hydrolysis resistance with simultaneous melt viscosity stability, and articles comprising them.

Polyesters, in general, have an excellent combination of moldability, mechanical properties, heat resistance, and chemical resistance and are widely used in the manufacture of molded materials such as connectors, relays, sensors, solenoids, switches and other electric and electronic parts. However, polyester compositions imparting both good hydrolysis resistance to produced articles and melt viscosity stability during melt processing have been difficult to achieve. U.S. Pat. No. 4,456,723 discloses polyester compositions comprising substantially water-free calcium phosphate for improving the tracking resistance of the polyester composition. U.S. Pat. No. 6,838,529 discloses a polybutylene terephthalate (PBT) polyester composition comprising polybutylene terephthalate (PBT), a glycidyl ester compound, a glycidyl ether compound, a catalyst, such that the carboxyl end group content of the polyester is at most 7 equivalents per ton, which imparts hydrolysis resistance to the composition. U.S. Pat. No. 7,008,983 discloses polyester compositions comprising a boron catalyst and a high level of epoxy component, which imparted hydrolysis resistance but also had the unwanted effect of increasing the melt viscosity of the compositions during melt processing. U.S. Pat. No. 7,893,141 discloses polyester compositions containing hydroxyapatite, to impart melt viscosity stability, an epoxy component, and a phosphorus containing compound, which ultimately inhibited the hydroxyapatite from stabilizing the melt viscosity of the composition. U.S. Pat. No. 6,048,626 discloses thermoplastic polyester compositions containing hydroxyapatite particles of specific particle diameters and specific surface areas and possibly an epoxy compound.

Thus, although polyester compositions having an epoxy component and/or hydroxyapatite have been disclosed, there remains a need for polyester compositions that exhibit both melt viscosity stability and a good hydrolysis resistance. Compared with known polyester compositions having an epoxy component and hydroxyapatite, polyester compositions having all of the following elements: —hydroxyapatite,
at least one epoxy component having two or more epoxy functional groups per molecule of the epoxy component, with a required amount of epoxy functionality relative to the polyester resin, and
a reinforcing agent
exhibit melt viscosity stability during melt processing and a good hydrolysis resistance in articles made of the compositions. The stabilized melt viscosity facilitates molding these compositions into articles with faster overall production rates because of decreased deposit build-up on the molding equipment during production. This in turn leads to reduced black speck contamination of the melt and to articles having fewer surface defects and ultimately to reduced production waste. Thus, polyester compositions having all four of these elements decrease production cost and waste and improve production time and overall yield.

To meet this need, described herein are compositions comprising:
a) 40 to 89 weight percent of at least one semi-aromatic polyester;
b) 10 to 50 weight percent of at least one reinforcing agent;
c) 0.5 to 5.0 weight percent hydroxyapatite;
d) 0.5 to 4.0 weight percent of at least one epoxy component having two or more epoxy functional groups per molecule of the epoxy component;
e) optionally, 0.5 to 15 weight percent of at least one toughener,
(d) and (e) having a combined epoxy functionality ranging from 40 and 500 milliequivalents per kilogram of the semi-aromatic polyester; and wherein:
when measured according to Test (A), each subsequent melt viscosity of the polyester composition is not greater than 160% of its initial melt viscosity; and
when measured according to Test (B), the tensile strength of exposed test bars comprising the polyester composition is at least 60% of that of unexposed bars comprising the identical composition; whereby: Test (A) comprises: —measuring initial melt viscosity of the polyester composition at five minutes after heating the polyester composition at a temperature between 30 and 45° C. above the melting point of the semi-aromatic polyester resin, and —measuring at least one subsequent melt viscosity of the polyester composition during an interval between greater than 5 minutes and 48 minutes while the temperature of the polyester composition is maintained between 30 and 45° C. above the melting point of the semi-aromatic polyester resin, wherein the measuring is done according to ISO 11443 at 1000 sec$^{-1}$; and
Test (B) comprises: —measuring tensile strength of unexposed test bars comprising the polyester composition; —exposing test bars comprising the same polyester composition for a duration of at least 25 hours to steam at 100 percent relative humidity, pressure of 2 atmospheres, and temperature of 121° C.; and —measuring at the end of the duration tensile strength of the exposed test bars, wherein the measuring is done according to ISO527-1 and all test bars have been molded according to ISO-2/1A.

Also described herein are processes for making these compositions and articles prepared from them.

Abbreviations

The claims and description herein are to be interpreted using the abbreviations and definitions set forth below.
"%" refers to the term percent.
"wt %" refers to weight percent
"mol %" or "mole %" refers to mole percent.
"hrs" refers to hours; "m" refers to minute; "s" refers to seconds.
"g" refers to grams.
"kg" refers to kilograms
"meq" refers to milliequivalents.
"Pa·sec" refers to Pascal·seconds.
"MPa" refers to Mega Pascals.
"MV-5" refers to initial melt viscosity.
"MV-X" refers to subsequent melt viscosity.

Definitions

As used herein, the article "a" indicates one as well as more than one and does not necessarily limit its referent noun to the singular.

As used herein, the term "about", when used to modify an amount or value, refers to an approximation of an amount or value that is more or less than the precisely designated amount or value. The precise value of the approximation is determined by what one of skill in the art would recognize as appropriate. The use of the term "about" conveys the idea that similar values can bring about equivalent results or effects.

As used herein, the terms "comprises," "comprising," "includes," "including," "has," "having" or any other variation of these, refer to a non-exclusive inclusion. For example, a process, method, article, or apparatus that comprises a list of elements is not limited to only the listed elements but may include other elements not expressly listed or inherent. Further, unless expressly stated to the contrary, "or" refers to an inclusive, not an exclusive, or. For example, a condition A or B is satisfied by any one of the following: A is true (or present) and B is false (or not present), A is false (or not present) and B is true (or present), and both A and B are true (or present).

As used herein, the term "epoxy component" refers to at least one epoxy containing molecule which has at least 2 epoxy functional groups per molecule of the epoxy component. "Epoxy component" refers to both an epoxy component comprising a single element having epoxy functionality and to an epoxy combination comprising two or more different elements having epoxy functionality.

As used herein, the terms "epoxy functionality", "functional" refer ONLY to the epoxy functional group in a molecule of the epoxy component; this is determined by the number of reactive sites per monomer.

As used herein, the term "combined epoxy functionality" refers to the sum of the milliequivalents of all epoxy functional groups present in any epoxy component and any toughener in the polyester composition. In other words, the milliequivalents of epoxy functionality in each epoxy component and the milliequivalents of epoxy functionality in each toughener in the polyester composition are added together to obtain the combined epoxy functionality in the polyester composition. Epoxy functionality is expressed as meq/kg of polyester resin. "Equivalents", "milliequivalents" refer to the number of moles or milli-moles or the molar equivalent of epoxy functional groups added per kilogram of polyester resin.

As used herein, the term "melt viscosity" refers to the viscosity of a polyester composition after heating the composition for some period of time at a temperature of 30-45° C. above the melting point of the semi-aromatic polyester resin in the composition and is measured according to ISO 11443 at a shear rate of 1000 s−1. The units for melt viscosity are Pascal·seconds (Pa·sec) and the measurements may be taken using a Dynisco LRC 7000 test Rheometer.

As used herein, the term 'initial melt viscosity' refers to the viscosity of a polyester composition after heating the composition for five minutes at a temperature of 30-45° C. above the melting point of the semi-aromatic polyester resin in the composition and is measured according to ISO 11443 at a shear rate of 1000 s−1. Initial melt viscosity is indicated herein as MV-5.

Heating the polyester composition for five minutes at a temperature of 30-45° C. above the melting point of the semi-aromatic polyester resin in the composition ensures a complete melt of the composition granules/pellets and the achievement of thermal equilibrium before measuring viscosity. The 5 minute period begins when heating starts.

As used herein, the term 'subsequent melt viscosity' refers to the viscosity of a polyester composition after heating the composition during an interval between greater than 5 minutes and 48 minutes at a temperature of 30-45° C. above the melting point of the semi-aromatic polyester resin in the composition and is measured according to ISO 11443 at a shear rate of 1000 s−1. At discrete intervals during the time period from greater than 5 minutes and 63 minutes, melt viscosity measurements may be taken, for example, at 5, or at 6, or at 7 minute intervals. Subsequent melt viscosity at "X" time is indicated by "MV-X", wherein X is greater than 5.

As used herein, the term "melting point" refers to the temperature of peak heat flow due to melting as measured by Differential Scanning calorimetry (DSC).

As used herein, the term "tensile strength" refers to that property of a material that is the maximum amount of stress that the material can take before failure and refers to a measurement made according to ISO 527-1 on tensile bars that have been injection molded according to ISO 527-2/1A. Tensile strength is measured in Pascals (Pa) or Megapascals (MPa).

As used herein, the term "unexposed test bars" refers to test bars molded according to ISO 527-2/1A and NOT exposed to those conditions specified below for exposed test bars before having tensile strength measured according to ISO 527-1.

As used herein, the term "exposed test bars" refers to test bars molded according to ISO 527-2/1A and exposed to the following conditions before having tensile strength measured according to ISO 527-1: steam in a pressure vessel at 100 percent relative humidity, pressure of 2 atmospheres, and temperature of 121° C. for at least 25 hours. Unexposed and exposed test bars are molded from an identical composition.

As used herein, the term 'Test A" refers to an inventor-developed test for determining melt viscosity stability of the compositions described herein. Test A compares the initial melt viscosity of the polyester composition with subsequent melt viscosities of the composition to yield a percentage of difference between the two. All melt viscosities are measured according to ISO 11443 at 1000 sec−1, As used herein, the term "Test B" refers to an inventor-developed test for indicating hydrolysis resistance of the polyester compositions described herein, measured by comparing the tensile strength of an unexposed test bar with that of an exposed test bar, in which both test bars are prepared from identical compositions. The decrease in tensile strength of the exposed test bar relative to the tensile strength of the unexposed test bar indicates relative hydrolysis resistance of the composition. The larger the decrease in tensile strength of the exposed test bar, relative to the unexposed test bar, the smaller the hydrolysis resistance of the composition. The more similar the tensile strengths of the exposed test bar and the unexposed test bar, the greater the hydrolysis resistance of the composition.

As used herein, the term "diphenolic epoxy condensation polymer" refers to a condensation polymer with epoxy functional groups, preferably as end groups, and a diphenol moiety within the polymer.

As used herein, the term "melt mixing" refers to a process in which heat is applied to a polymer and other materials physically combined together so that the polymer is heated above its melting point and the polymer's melting effects an essentially homogeneous melt mix or melt blend of the polymer and the other materials.

The other materials and the polymer may be dry blended, such as by tumbling, and then heated together at a temperature above the melting point of the polymer or the other materials may be added to the polymer as it is heated to its melting point or after the polymer has melted. The other materials need not be heated to above the melting point of the polymer.

As used herein, the term "melt processing" refers to transforming the melt mix or blend into articles by various operations known to those of skill in the art.

Ranges and Preferred Variants

Any range set forth herein expressly includes its endpoints unless explicitly stated otherwise. Setting forth an amount, concentration, or other value or parameter as a range specifically discloses all possible ranges formed from any possible upper range limit and any possible lower range limit, regardless of whether such pairs of upper and lower range limits are expressly disclosed herein. The compositions, processes and articles described herein are not limited to specific values disclosed in defining a range in the description.

The disclosure herein of any variation in terms of materials, methods, steps, values, and/or ranges, etc.—whether identified as preferred or not—of the processes, compositions and articles described herein specifically intends to include any possible combination of materials, methods, steps, values, ranges, etc. For the purpose of providing photographic and sufficient support for the claims, any disclosed combination is a preferred variant of the processes, compositions, and articles described herein.

DETAILED DESCRIPTION

Generally

Described herein are polyester compositions that simultaneously impart to articles made of them hydrolysis resistance in terms of tensile strength as well as facilitate melt viscosity stability during melt mixing of the compositions and comprise:

a) 40 to 89 weight percent of at least one semi-aromatic polyester;
b) 10 to 50 weight percent of at least one reinforcing agent;
c) 0.5 to 5.0 weight percent hydroxyapatite;
d) 0.5 to 4.0 weight percent of at least one epoxy component having two or more epoxy functional groups per molecule of the epoxy component;
3) optionally, 0.5 to 15 weight percent of at least one toughener,
(d) and (e) having a combined epoxy functionality ranging from 40 and 500 milliequivalents per kilogram of the semi-aromatic polyester resin; and wherein:

when measured according to Test (A) [see below], each subsequent melt viscosity of the polyester composition is not greater than 160% of its initial melt viscosity and when measured according to Test (B) [see below], the tensile strength of exposed test bars comprising the polyester composition is at least 60% of that of unexposed bars comprising the same polyester composition.

To obtain articles with good hydrolysis resistance, typically polyester resins are reacted with at least one epoxy component so as to cap the acid end groups of the polyester resin, termed end capping. Plus, to get articles with better hydrolysis resistance, it is known to end cap using a molar excess of epoxy functionality relative to the number of moles of acid end groups in the polyester resin. Such molar excess of epoxy component is also known to result in an undesirable increase in the viscosity of the composition during melt mixing, also termed melt processing.

It has not been known until now how to make polyester compositions that facilitate, during melt mixing or processing, a desirable melt viscosity stability as well as imparts hydrolysis resistance to articles molded from the compositions. Hydrolysis resistance as used here means that test bars exhibit relatively invariant tensile strength even after exposure to heat and humidity.

The polyester compositions described herein solve the following heretofore-unresolved technical problems: (1) Polyester compositions having decreased melt viscosity, which makes mold filling easier and more accurate, result in articles unsuitable for uses in hot, humid environments when good tensile strength is needed; and (2) Polyester compositions having epoxy functionality sufficient to give good tensile strength to molded articles exposed to heat and humidity create increased melt viscosity, which results in higher black speck formation in articles and thus higher production waste. Sufficient epoxy functionality is greater than two (2) epoxy groups per molecule of epoxy component.

Thus, the polyester compositions described herein include not only hydroxyapatite but also a reinforcing agent and a specific, recited concentration of epoxy component(s) such that each molecule of epoxy component has two or more epoxy functional groups. It is the specific combination of these claimed elements—a heretofore undisclosed, unknown, and not suggested combination—that solves the above stated technical problems. Put differently, it is this specific combination of elements that improves the melt viscosity stability of polyester compositions during melt processing and simultaneously imparts good hydrolysis resistance, in terms of retention of tensile strength, to articles made of the composition and exposed to heat and humidity.

The specific measures of this compound property are not random but express unambiguously the technical solution that results from combining into a polyester composition these three elements: hydroxyapatite, a reinforcing agent, and the specific claimed concentration of epoxy component(s) such that each molecule of epoxy component has two or more epoxy functional groups. To the point, the melt viscosity of the polyester compositions described herein, measured at greater than 5 and up to 48 minutes after applying certain high heat to the compositions, is not 60% greater than its initial melt viscosity, which is measured 5 minutes after first applying that heat. The tensile strength of test bars molded from a composition described herein and exposed to various test conditions for at least 100 hours is at least 60% of tensile strength of unexposed test bars molded of an identical composition.

This compound property of melt viscosity stability and hydrolysis resistance translates into stable flow of the melt in molds and retention of tensile strength in the finished article upon exposure to heat and humidity. Thus, this compound property facilitates articles that are not only made more economically and with less waste but also that are able to forestall hydrolytic breakdown of the polyester during hard use, such as long-term temperature and humidity exposure.

The polyester compositions described herein include all possible variations that can be made when the semi-aromatic polyester resin is selected from the group consisting of polyethylene terephthalate ("PET"), poly(trimethylene terephthalate) ("PTT"), and polybutylene terephthalate ("PBT"), polyethylene naphthalene ("PNT"), and combinations of these. In addition, when the semi-aromatic polyester resin is either PET or PBT, for each kilogram of resin: the quotient of milliequivalents of epoxy functionality over milliequivalents of acid end groups ranges from 2.5 to 10; and, the product of milliequivalents of acid end groups time milliequivalents of epoxy functionality ranges from 1000 to 5000. When the semi-aromatic polyester resin is PTT, for each kilogram of resin: the quotient of milliequivalents of epoxy functionality over milliequivalents of acid end groups ranges from 2.5 to 15; and, the product of milliequivalents of acid end groups times milliequivalents of epoxy functionality ranges from 200 to 3000.

Moreover, in any variation of these compositions having any of the semi-aromatic polyesters mentioned above, the reinforcing agent may be selected from the group consisting of glass fibers, glass beads, glass flake, mica, and combinations of these and/or the epoxy component may be selected from the group consisting of diphenolic epoxy condensation polymers, condensation products of glycidyl ethers and phenolic polymers, diglycidyl ether of bisphenol A polymers, tetraglycidyl ether of tetra(parahyroxyphenyl)ethane, and combinations of these.

In addition, any variation of these compositions having any of the polyester resins, and/or reinforcing agents and/or epoxy components mentioned above may have up to 10 weight percent of a toughener, which may be selected from the group consisting of copolymers of $C_1$ to $C_{10}$ alkyl acrylates, ethylene, and glycidyl methacrylate; and combinations of these. Further, for any variation of these compositions having any reinforcing agent, and/or any of the epoxy components and/or any of the tougheners mentioned above, when the semi-aromatic polyester resin is PBT, the exposure duration is 100 hours; for PTT, the exposure duration is 50 hours; and for PET, the exposure duration is 25 hours.

Also described herein are articles formed from any variation of these compositions and which, in particular, may in the form of an electronic part, an electrical part, an electrical part in an electric vehicle, an electrical part in a hybrid vehicle, a connector, a plug, a sensor, a relay, a solenoid, or a switch as well as in other forms known to those of skill in the art. Articles described herein include those for which a test plate of the article has a Comparative Tracking Index of at least 400.

Also described herein are two methods. The first is a method of making any of the variations of the polyester compositions described herein; and, the second is a method of maintaining melt viscosity stability while simultaneously retaining tensile strength in any variation of the polyester compositions described herein. Each of these methods comprises the step of:
melt-mixing, to form a polyester composition:
a) 40 to 89 weight percent of at least one semi-aromatic polyester;
b) 10 to 50 weight percent of at least one reinforcing agent;
c) 0.5 to 5.0 weight percent hydroxyapatite;
d) 0.5 to 4.0 weight percent of at least one epoxy component having two or more epoxy functional groups per molecule of epoxy component;
e) optionally, 0.5 to 15 weight percent of at least one toughener,
(d) and (e) having a combined epoxy functionality ranging from 40 and 500 milliequivalents per kilogram of the semi-aromatic polyester; and wherein: —when measured according to Test (A) [see below], each subsequent melt viscosity of the polyester composition is not greater than 160% of its initial melt viscosity and —when measured according to Test (B) [see below], the tensile strength of exposed test bars comprising the polyester composition is at least 60% of that of unexposed bars comprising the same polyester composition.

In any of the methods described herein, any variation of these polyester compositions having any of the polyester resins, any reinforcing agent, any epoxy component, and/or any of the tougheners mentioned above may be melt-mixed. Further, for any of these methods, when the semi-aromatic polyester resin is PBT, the exposure duration is 100 hours; for PTT, the exposure duration is 50 hours; and for PET, the exposure duration is 25 hours.

For all variations of these compositions, articles, and methods described herein, the property of melt viscosity stability has been determined using Test A and the tensile strength of exposed test bars has been determined using Test B. Test A compares the initial melt viscosity of the polyester composition with its subsequent melt viscosities. Test B compares the tensile strength of an unexposed test bar made of a composition described herein with the tensile strength of an exposed test bar of an identical composition. Thus, each test compares an initial state of the property with a subsequent state to calculate the percentage of that property that the composition retains. Such comparison thus shows the effect of adding the claimed combination of hydroxyapatite, reinforcing agent, and epoxy component into the composition.

Test (A) comprises: measuring initial melt viscosity of the polyester composition at five minutes after heating the polyester composition at a temperature between 30 and 45° C. above the melting point of the semi-aromatic polyester resin; and measuring at least one subsequent melt viscosity of the polyester composition during an interval between greater than 5 minutes and 48 minutes while the temperature of the composition is maintained between 30 and 45° C. above the melting point of the semi-aromatic polyester resin, the measuring being done according to ISO 11443 at 1000 $sec^{-1}$.

The initial melt viscosity is measured at five minutes after heating the polyester composition to temperature range mentioned above. At five minutes, regardless of semi-aromatic polyester resin, the polyester composition will be melted and uniformly mixed. The interval for measuring subsequent melt viscosity ranges between greater than 5 minutes and 48 minutes or up to 63 minutes, if PBT and 0.75 wt % of hydroxyapatite are used. This interval provides a sufficient period over which to demonstrate stability of the viscosity of the composition.

It is preferred that the initial melt viscosity of these polyester compositions be not greater than about 400 Pa·s, preferably not greater than about 350 Pa·s, more preferably not greater than about 250 Pa·s, when measured at 270° C. for polybutylene terephthalate) and poly(trimethylene terephthalate), and 290° C. for poly(ethylene terephthalate).

An initial melt viscosity greater than about 400 Pa·s can mean that the polyester composition has experienced a large melt viscosity increase while becoming melt mixed and indicates melt viscosity instability. Even though some polyester compositions may show little change between the initial melt viscosity (MV-5) measurement and a subsequent melt viscosity measurement taken at a long time interval, say, at 63 minutes, from when heat was first applied, whenever the initial melt viscosity is greater than about 400 Pa·s, such compositions are considered inherently melt unstable. The higher the initial melt viscosity of the composition, the more difficult it is to mold products; and it is highly unlikely that this greater initial melt viscosity will become less viscous over time.

Test (B) comprises: measuring tensile strength of unexposed test bars comprising the polyester composition; exposing test bars comprising the same polyester composition for a duration of at least 25 hours to steam at 100 percent relative humidity, pressure of 2 atmospheres, and temperature of 121° C.; and measuring at the end of the duration tensile strength of the exposed test bars, wherein the measuring is done according to ISO527-1 and all test bars have been molded according to ISO-2/1A. Exposure duration of the test bars may depend on the semi-aromatic polyester.

Polyester Compositions Described Herein a) Semi-Aromatic Polyester Resin

Semi-aromatic polyester resins described herein are derived from one or more aromatic dicarboxylic acids and one or more aliphatic or cycloaliphatic diols having two or more carbon atoms and mixtures of these.

Aromatic dicarboxylic acids are dicarboxylic acids having two carboxyl groups each attached to a carbon atom in a carbocyclic aromatic ring structure. It is not necessary that both functional carboxyl groups be attached to the same aromatic ring and where more than one ring is present; they can be joined by aliphatic or aromatic divalent radicals or divalent radicals such as —O— or —$SO_2$—.

Representative aromatic dicarboxylic acids include phthalic, terephthalic and isophthalic acids; bibenzoic acid; substituted dicarboxy compounds with two benzene nuclei such as bis(p-carboxyphenyl)methane; p-oxy-1,5-naphthalene dicarboxylic acid; 2,6-naphthalene dicarboxylic acid; 2,7-naphthalene dicarboxylic acid; 4,4'-sulfonyl dibenzoic acid and $C_1$-$C_{12}$ alkyl and ring substitution derivatives comprising one or more of terephthalic acid, isophthalic acid, and 2,6-naphthalene dicarboxylic acid. Preferred are terephthalic acid and isophthalic acid.

Examples of aliphatic or cycloaliphatic diols useful in the preparation of the polyester resins described herein include one or more of HO($CH_2$)$_n$OH (I); 1,4-cyclohexanedimethanol; HO($CH_2CH_2O$)$_m$$CH_2CH_2OH$ (II); and HO($CH_2CH_2CH_2CH_2O$)$_z$$CH_2CH_2CH_2CH_2OH$ (III), wherein n is an integer of 2 to 10, m on average is 1 to 4, and z is on average about 7 to about 40. (II) and (III) may be a mixture of compounds in which m and z vary but are not necessarily integers as m and z are averages.

Each kilogram of the semi-aromatic polyester resin should have fewer than 35, preferably fewer than 30, and more preferably fewer than 25, milliequivalents of carboxylic acid end groups. The milliequivalents of carboxylic acid end groups per kilogram of semi-aromatic polyester resin is also referred to as the acidity of the resin.

The concentration of carboxylic acid end groups affects hydrolysis resistance of the semi-aromatic polyester resin because the carboxyl acid end groups catalyze hydrolysis of the ester links in the polyester. See, e.g. Buxbaum, L H (1968) ANGEW. CHEM. INT. ED. ENGL. 7:182-90. Reducing the number of acid end groups retards hydrolysis of these ester links. The greater the concentration of acid end groups in the semi-aromatic polyester resin, the greater the concentration of epoxy functionality is needed in the polyester composition in order to react with the acid end groups and thereby provide hydrolysis resistance. As alluded to earlier, a high concentration of epoxy functionality arising from epoxy components having high concentrations of acid end groups may increase melt viscosity of the polyester compositions described herein and even raise the rate of melt viscosity increase during melt processing.

The milliequivalents of carboxylic acid end groups in the semi-aromatic polyester resin may be determined by any number of known titration methods. Commonly used is potentiometric titration, in which the semi-aromatic polyester resin is dissolved in an appropriate solvent and then titrated with a base, such as potassium hydroxide, to the inflection point or end point.

Preferably, the semi-aromatic polyester is selected from polyethylene terephthalate (PET), poly(trimethylene terephthalate) (PTT), polybutylene terephthalate (PBT), poly(ethylene 2,6-naphthoate) (PEN), and poly(1,4-cyclohexyldimethylene terephthalate) (PCT), and mixtures of these. More preferably the polyester resin is PET, PTT, PBT, and blends of these. Most preferably, the polyester resin is PBT. Examples of commercially available polyester resins include Crastin® PBT, Rynite® PET, and Sorona® PTT, available from E.I. du Pont de Nemours and Co., Wilmington, Del.

The polyester compositions described herein comprise at least one semi-aromatic polyester resin in an amount that ranges between 31 and 89 weight percent, preferably between 50 and 80 weight percent, and more preferably between 55 and 75 weight percent, of the total weight of the composition. Even though not expressly stated, the compositions described herein may comprise each and every possible range between 31 and 89 weight percent of semi-aromatic polyester resin.

a) Variant: Styrenic-Based Copolymers

The polyester composition according to the present invention may optionally contain one or more amorphous polymers to reduce warpage in the finished part. One or more of the thermoplastic polyesters described herein may be replaced by one or more styrenic-based copolymers, which may be grafted with acrylates or with butadienes. Examples of styrenic-based copolymers include without limitation styrene acrylonitrile copolymers (SAN), acrylonitrile butadiene styrenes (ABS) and acryl nitrile styrene copolymers (ASA). When present, the one or more styrenic-based copolymers may range up to 40 weight percent of the combined weight of the semi-aromatic polyester resin plus the styrenic-based copolymers in these compositions. Even though not expressly stated herein, all possible values up to 40 weight percent styrenic-based copolymer of the combined weight of semi-aromatic polyester resin styrenic-based copolymer are contemplated in these compositions.

b) Reinforcing Agent

The polyester compositions described herein include at least one reinforcing agent for improving mechanical strength and other properties, which may be a fibrous, tabular, powdery or granular material and may include glass fibers, PAN-derived or pitch-derived carbon fibers, gypsum fibers, ceramic fibers, asbestos fibers, zirconia fibers, alumina fibers, silica fibers, titanium oxide fibers, silicon carbide fibers, rock wool, powdery, granular or tabular reinforcing agents such as mica, talc, kaolin, silica, calcium carbonate, glass beads, glass flakes, glass microballoons, clay, wollastonite, montmorillonite, titanium oxide, zinc oxide, and graphite. Two or more reinforcing agents may be combined in these compositions; and although not expressly stated herein, these compositions may include every combination of reinforcing agents described herein.

Glass fibers, glass flakes, glass beads, mica, and combinations of these are preferred. Even though no specific type of glass fiber, flake, or bead is required, its sizing agent or coating should be neither highly acidic nor highly basic. Uncoated glass with high alkali content is not preferred as it may interfere with the effectiveness of the hydroxyapatite. Such a glass is termed "A glass" and is unsuitable unless coated. Preferred glass fiber is "E glass" fibers. Suitable glass fibers may be chopped strands of long or short glass fibers, and milled fibers of these.

The reinforcing agent may be processed on its surface with any known coupling agent (e.g., silane coupling agent, titanate coupling agent) or with any other surface-treating agent. The reinforcing agent for use herein may be coated or bundled with thermoplastic resins such as polyurethane and/or with thermosetting resin such as epoxy resin.

If used, fibers may have a circular or non-circular cross section. A fiber having a non-circular cross section refers to a fiber having a major axis lying perpendicular to a longitudinal direction of the fiber and corresponding to the longest linear distance in the cross section. The non-circular cross section has a minor axis corresponding to the longest linear distance in the cross section in a direction perpendicular to the major axis. The non-circular cross section of the fiber may have a variety of shapes including a cocoon-type (figure-eight) shape; a rectangular shape; an elliptical shape; a semielliptical shape; a roughly triangular shape; a polygonal shape; and an oblong shape. As will be understood by those skilled in the art, the cross section may have other shapes. The ratio of the length of the major axis to that of the minor access is preferably between about 1.5:1 and about 6:1. The ratio is more preferably between about 2:1 and 5:1 and yet more preferably between about 3:1 to about 4:1. Suitable fibers having a non-circular cross section are disclosed in EP Pat. No. 190001 and EP Pat. No. 196194. The fiber may be long fibers, chopped strands, milled short fibers, or other suitable forms known to those skilled in the art.

The reinforcing agent ranges from about 10 to about 50 weight percent, preferably about 15 to about 40 weight percent, and more preferably about 15 to about 30 weight percent of the total weight of the polyester compositions described herein. Even though not expressly stated herein, all possible ranges between 10 and 50 percent reinforcing agent of the total weight of the polyester composition are contemplated in these compositions.

c) Hydroxyapatite

The melt viscosity stabilizer in the these compositions has the chemical formula $Ca_5(PO_4)_3OH$ and the following chemical structure and is known to those of skill in the art as hydroxyapatite

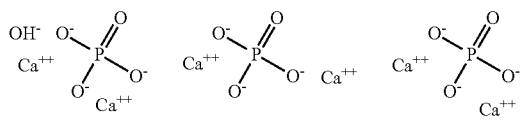

The chemical formula for hydroxyapatite is sometimes written as $Ca_{10}(PO_4)_6(OH)_2$ to denote that the crystal unit cell comprises two entities (a dimer).

The hydroxyapatite may have any particle size so long as that does not impede visual appearance or recited properties of the molded article, and is between about 0.001 and 500 microns, preferably 0.001 to 100 microns and even more preferably 0.001 to 10 microns.

The hydroxyapatite ranges from 0.5 to about 10 weight percent, preferably from about 0.75 and about 5 weight percent, and more preferably from about 1.0 and about 3.0 weight percent, of the total weight of the polyester compositions described herein. Although not expressly stated herein, all possible ranges between 0.5 and 10 weight percent hydroxyapatite of the total weight of the polyester composition are contemplated in these compositions. When hydroxyapatite is present in an amount of at least about 0.75 weight percent, each subsequent melt viscosity measured at an interval between greater than 5 minutes and 63 minutes according to Test (A) is not greater than 150% nor less than 40% of the initial melt viscosity.

d) Epoxy Component

Epoxy components suitable for use in the polyester compositions described herein include any epoxy component capable of reacting with an acid end group of the semi-aromatic polyester resins and having at least 2 epoxy functional groups per molecule of epoxy component. U.S. Pat. No. 6,974,846 and U.S. Pat. No. 7,008,983 disclose epoxy components that may be reacted with polyester resins to improve their hydrolysis resistance.

A preferred epoxy component is at least one diphenolic epoxy condensation polymer, which is known in the art, and includes condensation polymers of epichlorohydrin with a diphenolic compound. Also preferred is a 2,2-bis(p-glycidy) (oxyphenyl) propane condensation product with 2,2-bis(p-hydroxyphenyl)propane and similar isomers. Commercially available diphenolic epoxy condensation polymers include the EPON® 1000 resin series, from Momentive Specialty Chemicals.

Preferred epoxy components comprise at least two epoxy functional groups, more preferably at least three epoxy functional groups, and still more preferably at least four epoxy groups, per molecule of the epoxy component. The most preferred epoxy components comprise between two and eight epoxy groups per molecule of the epoxy component. The epoxy component should comprise not more than about 16, preferably not more than 10, and even more preferably not more than 6 epoxy functional groups per molecule of epoxy component.

The epoxy groups of the epoxy component preferably comprise glycidyl ethers, and even more preferably, glycidyl ethers of phenolic compounds. The epoxy components may be polymeric, oligomeric, or non-polymeric. An example of an epoxy component is a tetraglycidyl ether of tetra (para-hydroxyphenyl)ethane. An example of a commercially available epoxy component is Araldite®ECN 1299, available from Advanced Materials, Basel Switzerland. Another example is EPON® 1031 available from Momentive Specialty Chemicals, Inc.

Other epoxy components include epoxidized natural oils or fatty esters such as epoxidized soybean oil, epoxidized linseed/soybean oil, copolymers of styrene and glycidyl methacrylate, diglycidyl ethers of bisphenol A/bisphenol F, diglycidyl adducts of amines and amides, diglycidyl adducts of carboxylic acids, bis(3,4-epoxycyclohexylmethyl) adipate, vinylcyclohexene di-epoxide, epoxy phenol novolac and epoxy cresol novolac resins, epoxidized alkenes such as epoxidized alpha olefins, and epoxidized unsaturated fatty acids.

The epoxy component (d) ranges from 0.5 and 4.0 weight percent of the polyester compositions described herein. The toughener (e), if present, ranges from 0.5 and 15, preferably from 1 and 10, weight percent of the polyester compositions described herein. Even though not expressly stated herein, all possible ranges from 0.5 and 4.0 weight percent epoxy component and all possible ranges range 0.5 and 15 weight percent toughener, based on the total weight of the polyester composition, are contemplated in these compositions.

If these compositions have tougheners, the milliequivalents of epoxy functionality in the toughener must be included to calculate combined epoxy functionality. The combined epoxy functionality in the compositions that include at least one epoxy component and optionally at least one toughener ranges from 40 and 500 milliequivalents per kilogram of the semi-aromatic polyester resin. That is, the total epoxy functionality from all epoxy functional elements in the composition ranges from 40 and 500 milliequivalents per kilogram of the semi-aromatic polyester resin. Even though not expressly stated herein, all possible ranges of epoxy functionality from 40 and 500 milliequivalents per kilogram of the semi-aromatic polyester resin are contemplated in these compositions.

Epoxy Combinations

Besides single epoxy components, epoxy combinations comprising two or more, different elements having epoxy functionality may also be used in these polyester compositions. An example of an epoxy combination is: (i) diphenolic epoxy condensation polymer, and (ii) at least one epoxy component having at least two epoxy groups per molecule of the epoxy component. The preferred diphenolic epoxy condensation polymer is described above and exemplified by EPON® 1000 resin series. The preferred epoxy component is described above and exemplified by EPON® 1031.

In an epoxy combination, the epoxy component may be polymeric or non-polymeric, the latter being preferred. Epoxy combinations in these compositions range from 40 and 500, preferably from 50 and 300, more preferably from 60 and 200, and even more preferably from about 80 and 150, milliequivalents of epoxy functionality per kilogram of semi-aromatic polyester resin.

In an epoxy combination, the epoxy component provides about 1 to about 99%, preferably about 1 to about 80%, more preferably about 1 to about 60%, even more preferably about 10 to about 75%, and most preferably about 20 to about 50% of the epoxy functionality.

As used herein, the term "epoxy component" refers to both an epoxy component comprising a single element having epoxy functionality and to an epoxy combination comprising two or more different elements having epoxy functionality. The combined epoxy functionality from all elements having such functionality ranges from 40 and 500 milliequivalents per kilogram of the semi-aromatic polyester resin. Even though not expressly stated herein, all possible ranges of combined epoxy functionality ranging from 40 and 500 meq per kg of the semi-aromatic polyester resin are contemplated in these compositions.

Calculating Milliequivalents of Epoxy Functionality

Calculating the concentration of epoxy functionality of the at least one epoxy component (or epoxy combination) in these polyester compositions depends, among other things, upon 1) epoxy equivalent weight—a measure of the number of epoxy groups in the epoxy component; 2) the weight percent of the epoxy component in the semi-aromatic polyester resin; and 3) the epoxy equivalent weight of the toughener, which is a measure of the number of epoxy groups in the toughener, if present, and the weight percent of the toughener in the composition.

As stated above, the concentration of epoxy component (or epoxy combination) ranges from about 0.5 and 4 weight percent of the total weight of the polyester composition. However, when the epoxy component has more than two epoxy functional groups, its concentration in these compositions may be lower. For example, the concentration of an epoxy component having three epoxy functional groups per molecule of epoxy component can be less than that of an epoxy component having only two.

The milliequivalents of epoxy functionality from the epoxy component and, if present, the toughener, are calculated before the epoxy component and toughener are added to the composition.

Equation I calculates the milliequivalents of epoxy functionality for one epoxy component and a toughener per kilogram (meq/kg) of semi-aromatic polyester resin.

$$\left[ \frac{\text{wt \% epoxy } A}{(EEW \text{ of epoxy } A \times \text{wt \% } PE \text{ resin})} + \frac{\text{wt \% epoxy } T}{(EEW \text{ of epoxy } T \times \text{wt \% } PE \text{ resin})} \right] \times 1000 \times 1000, \quad \text{Equation 1}$$

wherein, wt % epoxy A indicates the weight percent of the epoxy component;

EEW indicates the Epoxy Equivalent Weight, which is defined as the mass in grams of the epoxy component (or toughener) that contains one mole of epoxy groups, measured according to ISO 3001;

wt % PE resin indicates the weight percent of the semi-aromatic polyester resin;

wt % epoxy T indicates the weight percent of the toughener.

When there is more than one epoxy component or toughener, the combined milliequivalents of epoxy functionality is the sum of the milliequivalents of epoxy functionality from all epoxy components and tougheners in the polyester composition.

Equation 2 calculates the combined milliequivalents of all epoxy components and tougheners, if present, per kilogram (meq/kg) of semi-aromatic polyester resin.

$$\sum \left[ \frac{\text{wt \% } Y_n}{(EEW \text{ of } Y_n \times \text{wt \% } PE \text{ resin})} \right] \times 1000 \times 1000 \quad \text{Equation 2}$$

wherein:

Σ indicates a summation of the calculated epoxy functionality according to Equation 1 above for each epoxy component and toughener; and $Y_n$ indicates the nth epoxy component or toughener in the polyester composition.

Epoxy components in these compositions must comprise sufficient epoxy functionality to provide about 40 to 500, preferably about 50 to 300, more preferably about 60 to 200, and even more preferably about 80 to 150 milliequivalents (meq), of combined epoxy functionality per kilogram (meq/kg) of semi-aromatic polyester resin.

e) Toughener

The polyester compositions described herein may optionally include at least one toughener, typically an elastomer having a relatively low melting point that is generally lower than 200° C. and preferably lower than 150° C., and with functional groups that can react with the carboxyl and hydroxyl groups of the semi-aromatic polyester resin (and optionally other polymers present).

Such functional groups of the toughener may include epoxy, carboxylic anhydride, hydroxyl (alcohol), carboxyl, and isocyanate, with epoxy and carboxylic anhydride being preferred and epoxy especially preferred. The toughener is typically prepared by grafting small molecules onto an existing polymer or by copolymerizing at least one monomer containing the desired functional group to make a polymeric toughener. For example, maleic anhydride may be grafted onto a hydrocarbon rubber using free radical grafting techniques. The resulting grafted polymer has carboxylic anhydride and/or carboxyl groups attached to it. An example of a copolymerized toughener occurs when polymerizing a co-polymer of ethylene and a (meth)acrylate monomer.

(Meth)acrylate as used herein refers to either an acrylate, a methacrylate, or a mixture of the two. Suitable (meth) acrylate functional compounds include (meth)acrylic acid, 2-hydroxyethyl (methacrylate, glycidyl (meth)acrylate, and 2-isocyanatoethyl (meth)acrylate. In addition to ethylene and a functional (meth)acrylate monomer, other monomers, such as vinyl acetate, unfunctionalized (meth)acrylate esters such as ethyl (meth)acrylate, -butyl (meth)acrylate, and cyclohexyl (meth)acrylate, may be polymerized into a toughener. Preferred toughening agents include those listed in U.S. Pat. No. 4,753,980, hereby incorporated herein by reference. Especially preferred tougheners are selected from the group of copolymers of $C_1$ to $C_{10}$ alkyl acrylates, ethylene, and glycidyl methacrylate; and combinations of these. These include copolymers having ethylene; glycidyl methacrylate; and ethyl acrylate, n-butyl acrylate, or methyl acrylate.

When present, the toughener preferably contains from about 0.5 to about 20, preferably from about 1.0 to about 10, more preferably about 7 to about 13, weight percent of repeat units derived from monomers containing functional groups. The toughener may have more than one type of repeat unit derived from functionalized monomer. Toughness of the composition is increased by adding more of the toughener and/or by upping the concentration of functional groups in the toughener but should not be increased so that cross-linking is induced in the polyester compositions described herein, especially before completing the article.

In addition, the toughener may be a thermoplastic acrylic polymer that is not a copolymer of ethylene and made by copolymerizing two or more of the following monomers: acrylic acid, acrylate esters (such as methyl acrylate, n-propyl acrylate, isopropyl acrylate, butyl acrylate, n hexyl acrylate, and n-octyl acrylate), methacrylic acid, and methacrylate esters (such as methyl methacrylate, n-propy) methacrylate, isopropyl methacrylate, n-butyl methacrylate (BA), isobutyl methacrylate, rt-amyi methacrylate, t-octyl methacrylate, glycidyl methacrylate (GMA) and the like. Preferred monomers for the preparation of a thermoplastic acrylic polymer toughener are methyl acrylate, n-propyl acrylate, isopropyl acrylate, n-butyl acrylate, n-hexyl acrylate, and/7-octyl acrylate. When derived from these monomers, the toughener may also be copolymerized with styrene, acrylonitrile, butadiene, isoprene, and the like. Some or all of the elements in these copolymers should preferably have a glass transition temperature of not higher than 0° C.

The thermoplastic acrylic polymer toughener may have a core-shell structure, in which the core has a glass transition temperature of preferably 0° C. or less and the shell has a glass transition temperature higher than that of the core. The core may be grafted with functional groups such as epoxy or carboxylic anhydride.

When present, the toughener preferably ranges from about 0.5 and about 15, and more preferably from about 1 and about 10, weight percent of the total weight of the compositions described herein. Tougheners that comprise epoxy functionality must be included in the above calculations for determining combined epoxy functionality.

Other Additives

The polyester compositions described herein may further comprise additional additives that include, but are not limited to, one or more of the following components as well as combinations of these: fillers, heat stabilizers, oxidative stabilizers, ultraviolet light stabilizers, one or more flame retardant agents, lubricants, plasticizers, flow enhancing additives, antistatic agents, coloring agents, nucleating agents, crystallization promoting agents, and other processing aids known in the field of compounding polymers.

The Combined Property of Melt Viscosity Stability and Hydrolysis Resistance

The property of melt viscosity stability is indicated by and measured as the difference between initial melt viscosity and subsequent melt viscosity of melt-mixed polyester compositions described herein. Hydrolysis resistance is indicated by tensile strength retention, which in turn is indicated by and measured as the difference between the tensile strength of exposed test bars vs that of unexposed test bars, which comprise an identical polyester composition described herein.

The combination of melt viscosity stability and tensile strength retention of exposed test bars is novel and driven by adding to a semi-aromatic polyester resin the specific combination of:

10 to 50 weight percent of at least one reinforcing agent;
0.5 to 5.0 weight percent hydroxyapatite;
0.5 to 4.0 weight percent of at least one epoxy component having two or more epoxy functional groups per molecule of the epoxy component,
with combined epoxy functionality ranging from 40 and 500 milliequivalents per kilogram of the semi-aromatic polyester resin, such that all weight percents are based on the total weight of the resultant composition.

The hydroxyapatite in these compositions is largely responsible for effecting melt viscosity stability and the combined epoxy functionality coupled with the reinforcing agent is largely responsible for effecting tensile strength retention after exposure to heat and humidity. However, the claimed, combined property results ONLY from balancing the effect brought about by the hydroxyapatite relative to that brought about by the epoxy functionality and the concentration of acid end groups in the semi-aromatic polyester resin. It is this balancing of competing effects that creates the novel and inventive, combined property, which is:

melt-mixed compositions described herein exhibit subsequent melt viscosity not greater than 160% of its initial melt viscosity AND exposed test bars exhibit at least 60% of the tensile strength of unexposed bars, all test bars containing an identical polyester composition described herein.

Relationship Between Epoxy Functionality, Melt Viscosity Stability, and Acid End Group Concentration The chemical interactions between the acid end groups of the semi-aromatic polyester resin and the epoxy functional groups are complex. Equation 3 calculates the ratio of: the preferred excess epoxy functionality relative to the concentration of acid end groups in these compositions, which depend on the semi-aromatic polyester resin.

$$\left[\frac{\text{meq of combined epoxy functionality}}{\text{kg of semi-aromatic polyester resin}}\right] \div \left[\frac{\text{meq of carboxylic acid end groups}}{\text{kg of semi-aromatic polyester resin}}\right] = 2.5 \text{ to } 15 \quad \text{Equation 3}$$

For PET or PBT, this ratio ranges from 2.5 to 10; for PTT, from 2.5 to 15.

To improve hydrolysis resistance, the concentration of combined epoxy functionality (see Equation 2) in these compositions should be greater than the concentration of acid end groups in the semi-aromatic polyester resin as described by Equation 3.

For the compositions described herein, Equation 4 characterizes the overall preferred range of multiplicative effects on melt viscosity created between the acid end groups of the semi-aromatic polyester resin and the epoxy functional groups, which effects vary depending on the semi-aromatic polyester resin used. If the product in equation 4 is high, that is above 4000 for PET or PBT and 3000 for PPT, then the recited melt viscosity stability may not be attainable due to the multiplicative effect of the concentration of combined epoxy functionality and concentration of acid end groups on the melt viscosity stability.

$$\frac{\text{meq of combined epoxy functionality} \times \text{meq of carboxylic acid end groups}}{\text{kg of semi-aromatic polyester resin}} = 200 \text{ to } 4000 \quad \text{Equation 4}$$

For PET or PBT, the value of Equation 4 ranges from 1000 to 4000; for PTT, from 200 to 3000.

It is important to note that, for PET or PBT resins, when Equation 3 is greater than 10 and Equation 4 greater than 5000; or for PTT resin, when Equation 3 is greater than 15 and Equation 4 greater than 3000, then addition of the claimed amount of hydroxyapatite may not create the claimed melt viscosity stability.

It is also important to note that, for PET or PBT resins, when Equation 3 ranges from 2.5 to 10 and Equation 4 ranges from 1000 to 5000, or for PTT resin, when Equation 3 ranges from 2.5 to 15 and Equation 4 ranges from 200 to 3000, then the recited amount of hydroxyapatite should result in the recited melt viscosity stability Polyester compositions exhibiting the combined property of melt viscosity stability and tensile strength imparted by this combination of elements are identified using Test A and Test B as recited in the claims and described herein.
Polyester compositions will have the unique combination of hydrolysis resistance and melt viscosity stability if the subsequent melt viscosity of the polyester compositions is not greater than 160% of the polyester compositions initial melt viscosity using test A, and test bars comprising the polyester compositions are exposed to conditions in Test B and after exposure, retains 60% of unexposed test bars tensile strength.

Test A comprises: —measuring initial melt viscosity of the polyester composition at five minutes after heating the polyester composition at a temperature between 30 and 45° C. above the melting point of the semi-aromatic polyester; and —measuring at least one subsequent melt viscosity of the polyester composition during an interval between greater than 5 minutes and 48 minutes while the temperature of the polyester composition is maintained between 30 and 45° C. above the melting point of the semi-aromatic polyester, wherein measuring is done according to ISO 11443 at 1000 sec$^{-1}$.

Test B comprises: —measuring tensile strength of unexposed test bars, molded according to ISO-2/1A, and comprising the polyester composition; —exposing the test bars for a duration of at least 25 hours to steam at 100 percent relative humidity, pressure of 2 atmospheres, and temperature of 121° C.; and —measuring at the end of the exposure duration tensile strength of the test bars, wherein the measuring is done according to ISO527-1.

Test B is a wet test method in which test bars comprising the polyester compositions are exposed to a humid environment for a set time period. This differs completely from heat aging tests carried out in air ovens at elevated temperature such as described in UL 746B or IEC60216, in which test bars are typically exposed to dry air heated above 100° C. Heat aging testing provides no measurement of the hydrolytic stability of the composition making up the test bar.

Polyester compositions described herein by definition exhibit during melt viscosity testing a melt viscosity that does not increase over its initial melt viscosity by more than 60%. That is, these compositions will maintain a melt viscosity within 160% of their initial melt viscosity (MV-5) while being heated for 48 minutes at a temperature 30 to 45° C. above their melting points under shear conditions (1000 s−1). This means, for example, that, if the initial melt viscosity of a composition described herein was 100 Pa·sec, then its subsequent melt viscosity will not increase to greater than 160 Pa·sec during the entire melt viscosity testing period, i.e. up to 48 minutes after first applying heat.

Excluding Compounds Having pH Outside 6 to 8

Excluding certain acidic or basic compounds from the polyester compositions described herein may be required. As used herein, the term "acidic or basic compound" includes acceptor-donor substances such as Lewis acids or bases, Bronstead acids or bases as well as compounds that release or generate acidic or basic compounds during melt processing or in the final product. For descriptions of acidic or basic compounds, see March, J (1997) *Advanced Organic Chemistry* (Chapter 8) in SERIES IN ADVANCED CHEMISTRY, McGraw-Hill; and Bukowski and Bukowski (2002) ORGANIC PROCESS RESEARCH AND DEVELOPMENT, 6: 234-237; *Epoxy Resins* (1986) (Volume 6) in ENCYCLOPEDIA OF POLYMER SCIENCE AND ENGINEERING, John Wiley and Sons.

Compounds exhibiting pH of 8 or greater (basic) or 6 or less (acidic) or which release or generate compounds of such pH during melt processing or in the final article should be excluded from the polyester compositions described herein. This is because, when the polyester compositions described herein have pH outside the range of 6 to 8, the recited amount of hydroxyapatite and epoxy functionality plus reinforcing agent may be unable to effect the recited, combined property of melt viscosity stability and hydrolysis resistance.

One of skill in the art can determine without undue experimentation whether a certain acidic or basic compound negatively affects the melt viscosity stability and hydrolysis resistance of these compositions. Identifying whether certain compounds should be excluded from these compositions depends on determining the pH of an aqueous solution, suspension, or dispersion in which the compound is included. To determine pH, a solution, suspension, or dispersion of the compound is prepared by adding from about 10 g/L to about 100 g/L of the compound to deionized water. The compound is stirred in water at 20° C. and the pH measured by any suitable method known in the art.

Compounds that either exhibit a pH between 6 and 8, preferably between 6.5 and 7.5, or are essentially insoluble in water or do not generate acidic or basic compounds during melt-mixing or molding are expected not to vitiate the balancing effect of the hydroxyapatite, epoxy functionality and reinforcing agent in these compositions and, consequently, need not be excluded from these compositions. However, compounds that are water-insoluble but capable of being hydrolysed by water into acidic or basic compounds may so vitiate the balancing effect and should be excluded.

The literature has disclosed some compounds that should be excluded from these compositions, which include phosphorus containing flame retardants and flame retardant synergists, such as phosphorous (0) flame retardants, red phosphorus, phosphorous (III) and phosphorous (IV) compounds, organophosphites, organo phosphoric acids, organo phosphonic acids, organo phosphinic acids, and polymeric/ligomeric derivatives of these compounds. The following should also be excluded: phosphorous acids, organo phosphates and diphosphate esters, such as triphenyl phosphate, tetraphenyl bisphenol A-diphosphate (BPA-DP), resorcinol bis(diphenyl phosphate) (RDP), organo phosphonate esters, and organo phosphinate esters.

Other excluded compounds include inorganic alkali metals, alkali earth metals, zirconium, aluminium, boron, and ammonium salts of phosphoric acids, phosphonic acids, phosphinic acids, and polymeric or oligomeric derivatives of these compounds: Exolit OP1230, ammonium phosphate and polyphosphate, are specific examples.

Additional excluded compounds are organophosphinates and their salts, organophosphonates and their salts, melamine flame retardants and their derivatives, melamine cyanurate, melamine phosphate, polyphosphate, pyrophosphate, dimelamine phosphate, and the like. Specific examples include Melapur® MC25, MC50, MCXL; Melapur 200, 200/70, 200FF, and Melapur MP.

Metal oxides generate acidic or basic compounds during melt processing and include calcium oxides, magnesium oxides, metal hydroxides (aluminium, magnesium) and should be excluded from these compositions. Others to be excluded are: flame retardant synergists that are metal salts, such as sodium antimonate; metal salts of lubricants, nucleants, fatty acids such as metal stearates, sodium stearate and montanates, metal salts of ethylene/methacrylic acid copolymers such as sodium and zinc Surlyn® ionomers, and metal salts of borates such as sodium tetraborate. Other possibly excluded compounds include minerals and fillers, e.g. calcium carbonate, kaolin, barium sulphate, and hydrotalcite.

The exclusion of a compound from these compositions can depend on its concentration. Specifically, when the concentration of a compound is low enough to ensure that its pH does not vitiate the balancing effect brought about by the claimed combination of hydroxyapatite, epoxy functionality and reinforcing agent, then that compound need not be excluded.

Making Polyester Compositions and Articles Described Herein

The polyester compositions described herein are made by a process of melt-mixing, to form the composition:
a) 40 to 89 weight percent of at least one semi-aromatic polyester;
b) 10 to 50 weight percent of at least one reinforcing agent;
c) 0.5 to 5.0 weight percent hydroxyapatite;
d) 0.5 to 4.0 weight percent of at least one epoxy component having two or more epoxy functional groups per molecule of epoxy component;
e) optionally, 0.5 to 15 weight percent of at least one toughener,
(d) and (e) having a combined epoxy functionality ranging from 40 and 500 milliequivalents per kilogram of the semi-aromatic polyester; and wherein: —when measured according to Test (A), each subsequent melt viscosity of the polyester composition is not greater than 160% of its initial melt viscosity and —when measured according to Test (B), the tensile strength of exposed test bars comprising the polyester composition is at least 60% of that of unexposed bars comprising the same polyester composition; whereby:

Test (A) comprises: —measuring initial melt viscosity of the polyester composition at five minutes after heating the polyester composition at a temperature between 30 and 45° C. above the melting point of the semi-aromatic polyester, and —measuring at least one subsequent melt viscosity of the polyester composition during an interval between greater than 5 minutes and 48 minutes while the temperature of the polyester composition is maintained between 30 and 45° C. above the melting point of the semi-aromatic polyester, wherein the measuring is done according to ISO 11443 at 1000 sec$^{-1}$; and Test (B) comprises: —measuring tensile strength of unexposed test bars comprising the polyester composition; —exposing test bars comprising the same polyester composition for a duration of at least 25 hours to steam at 100 percent relative humidity, pressure of 2 atmospheres, and temperature of 121° C.; and —measuring at the end of the duration tensile strength of the exposed test bars, wherein the measuring is done according to ISO527-1 and all test bars have been molded according to ISO-2/1A.

The processes described herein include any and all variations described above for these compositions, including but not limited to variations in composition elements, preferred ranges for compositional elements and for epoxy functionality and for exposure durations, etc.

The polyester compositions described herein are melt-mixed blends, wherein all the polymeric components are well-dispersed within each other and all the non-polymeric ingredients are well-dispersed such that the blend forms a unified whole. They are made by blending the components in any order or combination, at any convenient temperature as long as the polymeric ingredients are in the melt or molten state. Blending or mixing temperatures are easily determined by one of knowledge in the art.

Any melt-mixing method may be used to combine the polymeric components and non-polymeric components. For example, the polymeric components and non-polymeric ingredients may be added to a melt mixer, such as a single or twin-screw extruder; a blender; a single or twin-screw kneader; or a Banbury mixer, either all at once through a single step addition, or in a stepwise fashion, and then melt-mixed. When adding the polymeric components and non-polymeric ingredients in a stepwise fashion, part of the polymeric components and/or non-polymeric ingredients are first added and melt-mixed with the remaining polymeric components and non-polymeric ingredients being subsequently added and further melt-mixed until a well-mixed composition is obtained. The melt-mixing can result in pellets, which can be extruded or molded into articles.

The polyester compositions described herein may be shaped into articles using methods known to those skilled in the art, such as injection molding, blow molding, injection blow molding, extrusion, thermoforming, melt casting, vacuum molding, rotational molding, calendar molding, slush molding, filament extrusion and fiber spinning Articles Comprising the Compositions Described Herein The polyester compositions described herein may be used in the preparation of molded or extruded articles such as components for automobiles, including various electric and electronic components, such as connectors, solenoids, coil formers, bobbins, and housings for electric and electronic components such as sensors, Engine Control Units ("ECUs"), fuses and electrical junction boxes for photovoltaic panels.

The electrical and electronic parts used in some automobile designs, especially fully electric and hybrid vehicles, should also have enhanced resistance to tracking. Tracking is the current flowing on the surface of an insulator between two electrodes caused either through pollution or degradation of the insulator. Tracking resistance is a way to measure the ability of an insulator to prevent such problems. The Comparative Tracking Index (CTI) of a molded part represents the relative resistance of solid electrical insulating material to tracking, that is, electrical breakdown at the surface of the material. According to IEC 60112, CTI of a material surface is measured for voltages up to 600 volts ("V") when the surface is exposed under electrical stress to water comprising various contaminants A Comparative Tracking Index of greater than 400 is high and considered essential for parts in electric and hybrid vehicles to accommodate the higher power requirements placed on these parts. For example, electrical and electronic components in such vehicles must withstand voltages greater than 400, and preferably greater than 500V, over a tenfold increase compared to voltages in gas-powered vehicles having 24V lead acid batteries.

Examples

The Examples (E) and Comparative Examples (C) below are intended only to further illuminate and not to limit the scope of the compositions, methods, and articles described herein.

Materials

Glass Fiber A: chopped glass fiber, 9.5-11.5 µm diameter, available as NEG 187, from Nippon Electric Glass Co., Ltd., Japan.

Glass Fiber B: chopped glass fiber, 10 µm diameter, available as OCV952 from OCV, Europe.

PBT: polybutylene terephthalate with melt flow rate (MFR) from 41 to 55 g/10 min (measured according to ISO1133, 250° C., 2.16 kg), a carboxylic acid end group concentration of 19 meq/kg, available as Crastin® from E.I. DuPont de Nemours and Company, Wilmington, Del. [DuPont]; same as poly(1,4-butylene) terephthalate.

PET: polyethylene terephthalate having an intrinsic viscosity from 0.63 to 0.66 dl/g, a carboxylic acid end group concentration of 18 meq/kg, c available from SASA, Turkey.

PTT: polytrimethylene terephthalate having an intrinsic viscosity from 1.01 to 1.03 dl/g, a carboxylic acid end group concentration of 8 meq/kg, available as Sorona® EP from DuPont.

Toughener: reactive elastomeric terpolymer of ethylene/n-butyl acrylate/glycidyl methacrylate having a density of 0.94 g/cm$^3$, a melt flow rate (ASTM D1238; 190° C./2.16 kg) of 12 g/10 min., a melting point of 72° C., and an epoxy equivalent weight of about 2705 g, available from DuPont.

MF Epoxy A (Epikote® 1002): An epoxy component having an average of about two epoxy functional groups per molecule produced from diglycidyl ether and bisphenol A with an average epoxy equivalent weight of 650 g/mol (ISO 3001) and a density of 1.19 g/cm$^3$ (ASTM D792), available from Momentive Specialty Chemicals, Inc. [Momentive].

MF Epoxy B—(Epon® 1031): An epoxy component having >2 to <8 epoxy functional groups per molecule produced from epichlorohydrin and tetraphenylol ethane, an average epoxy equivalent weight of 212 g/mol, and a density of 1.19 g/cm$^3$ (ASTM D792), available from Momentive.

MF Epoxy C—(Araldite® ECN 1299): an epoxy cresol novolac resin with an average Epoxy Equivalent Weight of 205-230 g/mol (ISO 3001); and an average of about 5.5 epoxy groups per molecule, available from Huntsman Advanced Materials, Basel, Switzerland.

Hydroxyapatite (anhydrous)—$Ca_5(PO_4)_3(OH)$: having pH of 6.8-7.5 (measured by dispersing 100 g/L in water at 20° C.).

β-phosphate tricalcium (anhydrous)—$Ca_3(PO_4)_2$: having pH of 8-9 (100 g/L 20° C.).

Dicalcium Phosphate (anhydrous)—$CaHPO_4$: having pH of 6-8 (100 g/L 20° C.).

Monosodium phosphate (anhydrous)—$NaH_2PO_4$: having pH of 4.5 (10 g/L 20° C.).

Monocalcium phosphate (anhydrous)—$Ca(H_2PO_4)_2$: having pH of 3 (10 g/L 20° C.).

Dicalcium pyrophosphate (anhydrous)—$Ca_2P_2O_7$: having pH of 6.0-8.0 (100 g/L 20° C.).

Trisodium Phosphate (anhydrous)—$Na_3PO_4$: having pH of 11.5-12.5 (10 g/L 20° C.).

$Ca_3(PO_4)_2$; $CaHPO_4$; $NaH_2PO_4$; $Ca(H_2PO_4)_2$; and $Ca_2P_2O_7$,$Na_3PO_4$ are commercially available.

Calcium Sulfate (anhydrous) $CaSO_4$: pH of 7 (100 g/L 20° C.), commercially available.

Hydrotalcite: magnesium/aluminium-hydrotalcite of formula $Mg_6A_{12}(CO_3)(OH)_{16}.4(H_2O)$ having pH of 7-9 (20 g/L 20° C.), available from BASF Schweiz AG, Switzerland [BASF].

Sodium tetraborate decahydrate: having pH 9.2 (10 g/l) available from Sigma-Aldrich.

Flame Retardant—Fyrolflex® RDP-LT: a resorcinol bis (diphenyl phosphate) flame retardant available from ICL-IP Europe B.V., The Netherlands.

FR Synergist—Melapur® MC25: melamine cyanurate flame retardant synergist, pH 5-6 (10% suspension 20-25° C.), available from BASF.

Organic phosphinate—Exolit® OP1230: aluminum salt of diethylphosphinic acid having a pH 5 (suspension 20° C., 10 g/L), available from Clariant, Del.

Barium Sulfate: having pH of about 9 (10% suspension 20-25° C.), commercially available.

PTFE: Polytetrafluoroethylene granular molding powder, available from DuPont.

SAN: Styrene acrylonitrile polymer with MVR 220° C./10 kg ISO1133 22 cm3/10 min, from Styrolution.

Lubricant: Pentaerithritol tetrastearate lubricant, available from Oleon NV, Belgium.

Antioxidant—(Irganox® 1010): a sterically hindered phenolic antioxidant, supplied by Ciba Specialty Chemicals, Tarrytown, N.Y., USA.

Plasticizer: a polyethylene glycol di-2-ethylhexoate ester plasticizer having a boiling point of 379° C. (760 mmHg), available from Hallstar Company (Plasthall® 809)

Talc: Magnesium silicate hydrate, available from Barrets Minerals Inc., USA

Methods

Polyester Composition Preparation

The polyester compositions of the Examples and Comparative Examples were prepared by melt mixing the ingredients by one of the methods described below. Ingredient quantities listed in the tables are given in weight percent on the basis of the total weight of the polyester composition.

Compounding Method A

The reinforced PBT based polyester compositions in tables 3 to 7, and tables 10 to 14 were prepared by melt mixing the ingredients listed in the Tables in a 40 mm twin screw extruder (Berstorff ZE40) operating with barrel temperatures settings of about 250° C. and screw speed settings of about 250 rpm. Extrusion throughput was around 110 kg/hour and measured melt temperatures by hand were in the range 270° C. to 300° C.

Glass fibers were added to the melt through a screw feeder. When liquid resorcinol diphosphate was added, (Tables 11, 13 and 14), it was fed to the melt through a liquid pump feeder. The polyester composition was extruded in the form of laces or strands, cooled in a water bath, chopped into granules and placed into sealed aluminum lined bags in order to prevent moisture pick up. The cooling and cutting conditions were adjusted to ensure that the materials were kept below 0.1% by weight moisture content. Prior to molding, the samples were pre-dried to less than 0.02% by weight moisture level.

Compounding Method B

The polyester compositions in tables 1 to 2, and 8 to 9 were prepared by melt mixing the ingredients listed in the tables in a 30 mm twin screw extruder (Coperion ZSK30) operating with barrel temperatures settings of about 250° C. and screw speed settings of about 250 rpm. Extrusion throughput was around 20 kg/hour and measured melt temperatures by hand were in the range 290° C. to 300° C. When used, glass fibers were added to the melt through a screw feeder. Extrusion, chopping and pre-drying were as described in Method A.

Compounding Method C

The reinforced PET polyester compositions in table 15 were prepared by melt mixing the ingredients listed there in a 40 mm twin screw extruder (Berstorff ZE40) operating with barrel temperatures settings of about 280° C. and screw speed settings of about 250 rpm. Extrusion throughput was around 90 kg/hour and measured melt temperatures by hand were about 300° C. Glass fibers were added to the melt through a screw feeder. Extrusion, chopping and pre-drying were as described in Method A.

Melt Viscosity Measurement

Prior to melt viscosity measurements, granules/pellets of the polyester composition as prepared by methods A, B or C above were dried at 120° C. for 4 hours in a vacuum dryer to a moisture level below 0.02 wt % percent. Melt viscosity was determined according to ISO 11443 at a shear rate of 1000 s−1. For PBT and PTT, the temperature of 270° C. was used. For PET, the temperature of 290° C. was used.

A test sample of the polyester composition to be tested was introduced into a Dynisco LRC 7000 test rheometer barrel and heating started. At five minutes from when heating was started, the initial melt viscosity indicated as MV-5 was measured. The five minutes duration after heating gives the polyester composition the time necessary to reach thermal equilibrium.

After the initial melt viscosity measurement, the temperature of the polyester composition was maintained at the claimed temperature for the specific polyester resin used in the polyester composition. Subsequent melt viscosities of the polyester composition were measured at various time intervals from after 5 minutes up to 63 minutes. Such time intervals include 10 minutes after heating started, which is indicated in the tables as MV-10; 16 minutes after heating started and is MV-16; 21 minutes after heating started and is MV-2; 26 minutes after heating started and is MV-26; 32 minutes after heating started and is MV-32; 37 minutes after heating started and is MV-37; 39 minutes after heating started and is MV-39; 42 minutes after heating started and is MV-42; 43 minutes after heating started and is MV-48; 53 minutes after heating started and is MV-59; and 63 minutes after heating started and is MV-63.

Subsequent melt viscosity measurements taken at these intervals were compared to the initial melt viscosity of the identical polyester composition. A ratio of each subsequent melt viscosity over the initial melt viscosity was calculated and multiplied by 100% according to Equation 5 to yield the percentage that each subsequent melt viscosity achieved relative to the initial melt viscosity:

$$\frac{\text{Subsequent Melt Viscosity }(SMV)}{\text{Initial Melt Viscosity }(MV\text{-}5)} \times 100\% = \%\text{-age } MV\text{-}5, \quad \text{Equation 5}$$

wherein %-age MV-5 is the Percentage of Initial Melt Viscosity that the subsequent melt viscosity achieved.

For example, if a subsequent melt viscosity of a polyester composition were measured at 32 minutes after heating, denoted as MV-32, and found to be 135 Pa·sec, and the initial melt viscosity had been measured as 100 Pa·sec, calculating this exemplary MV 32, according to Equation 5, gives:

$$\frac{MV\text{-}32}{(MV\text{-}5)} = \frac{135}{100} \times 100\% = 135\% \text{ of } MV\text{-}5.$$

Thus, the subsequent melt viscosity at 32 minutes (MV-32) of this composition was 135% of the initial melt viscosity (MV-5), which means that this composition had become more viscous by 35% at 32 minutes after heating, relative to the initial melt viscosity.

Conversely, if the subsequent melt viscosity of this composition had been 90 Pa·sec, and therefore less than the initial melt viscosity of 100 Pa·sec, then calculating this exemplary MV 32, according to Equation 5, gives:

$$\frac{MV\text{-}32}{MV\text{-}5} = \frac{90}{100} \times 100\% = 90\% \ MV\text{-}5.$$

In this case, the subsequent melt viscosity at 32 minutes after heating was only 90% of the initial melt viscosity, which means that this composition had become 10% less viscous by 32 minutes after heating.

Hydrolysis Resistance

Hydrolysis resistance of the polyester composition was determined by molding two sets of test bars according to ISO 527-2/1A and then exposing one set of the test bars to steam in a pressure vessel, measuring the tensile strength of each set of test bars and then comparing the tensile strength of the exposed test bars to that of the unexposed bars. Tensile strength was tested at a testing speed of 5 mm/min for glass reinforced polyester compositions and 50 mm/min for unreinforced polyester compositions.

Prior to injection molding, pellets of the polyester composition were dried to a moisture level below 0.02 wt %. For compositions having PBT or PTT as the semi-aromatic polyester resin, the mold temperature was 80° C. and the melt temperature was 250° C. For compositions having PET as the semi-aromatic polyester resin, the mold temperature was 130° C. and the melt temperature was 280° C.

Two different pressure vessels were used to heat age the test bars.

Five molded test bars were heat aged in steam in a first pressure vessel at a temperature of 118° C., greater than 70% relative humidity, and a pressure of 1.8 atmospheres ("atm"). The duration of exposure varied depending upon the semi-aromatic polyester resin and if glass reinforcing agent were added. The duration of exposure for glass reinforced, PBT compositions was 150 hours; for glass reinforced PTT compositions, 100 hours; for glass reinforced PET compositions, 75 hours; and for unreinforced PBT compositions, 50 hours. The five exposed test bars were removed from the pressure vessel and allowed to cool to room temperature. Tensile strength of the five exposed test bars was then measured according to ISO 527-1 using a Zwick tensile instrument at a testing speed of 5 mm/min for glass reinforced specimens and 50 mm/min for unreinforced specimens. The average tensile strength values obtained from the five exposed test bars are given in the tables as tensile strength determined at 150 hours, 100 hours, or 75 hours. The average tensile strength of the five exposed test bars and the average tensile strength of the five unexposed test bars were measured. Then, a ratio of average, exposed tensile strength relative to average, unexposed tensile strength was calculated and multiplied by 100% according to Equation 6 to yield the Percentage of Retained Tensile Strength. The tensile strength results using the first pressure vessel are shown in the tables as TS-1.

Tensile strength results using a second pressure vessel, a CertoClav Multicontrol 12/18L manufactured by CertoClav Sterilizer Gmbh, Austria, were obtained by heat aging five molded test bars in steam at a temperature of 121° C., 100% relative humidity, and a pressure of 2.0 atmospheres ("atm"). The duration of exposure varied depending upon the semi-aromatic polyester resin and if glass reinforcing agent were added. The duration of exposure for glass reinforced, PBT compositions was 100 hours; for glass reinforced PTT compositions, 50 hours; and for glass reinforced PET compositions, 25 hours. The five exposed test bars were removed from the pressure vessel and allowed to cool to room temperature. Tensile strength of the five exposed test bars was then measured according to ISO 527-1 using a Zwick tensile instrument at a testing speed of 5 mm/min for glass reinforced specimens and 50 mm/min for unreinforced specimens. The average tensile strength values obtained from the five exposed test bars are given in the tables as tensile strength determined at 100 hours, 50 hours, or 25 hours. The average tensile strength of the five exposed test bars and the average tensile strength of the five unexposed test bars were measured. Then, a ratio of average, exposed tensile strength relative to average, unexposed tensile strength was calculated and multiplied by 100% according to Equation 6 to yield the Percentage of Retained Tensile Strength. The tensile strength results using the second pressure vessel are shown in the tables as TS-2.

$$\frac{\text{Exposed Tensile Strength}}{\text{Unexposed Tensile Strength}} \times 100\% = \text{\%-age of Retained Tensile Strength,}$$ Equation 6 wherein:
Exposed Tensile Strength is the average tensile strength of a set of test bars made of a specific polyester composition, exposed to temperature, humidity and pressure for a certain duration;
Unexposed Tensile Strength is the average tensile strength of a set of unexposed test bars made of the identical polyester composition;
%-age Retained Tensile Strength, denoted as %-age Retained TS, is that percentage of the unexposed tensile strength that the exposed test bars continue to exhibit.

The Percentage of Retained Tensile Strength is the measurement of hydrolysis resistance.

Comparative Tracking Index (CTI)

The Comparative Tracking Index was measured according to IEC 60112 on 20×30×4 mm thick molded test samples cut from the end tabs of ISO-2/1A tensile bars. Tables 6 and 7 show that adding at least 0.5 weight percent hydroxyapatite to polyester compositions increased the CTI to greater than 400.

Polyester Acidity

About 1.4 g of the semi-aromatic polyester resin for which acidity is to be determined is dissolved in o-cresol solvent and titrated with 0.03N KOH in ethanol with potentiometric determination of the end point. This end point was corrected by subtracting the end point of a blank sample, which was determined by titrating the pure solvent by the same method.

Discussion

Legend for all Tables:
"C" indicates Comparative Examples; "E", Examples.
NM: Not Measured, either because of high sample viscosity or all material was consumed before end of experiment.
NT: not tested; tensile bars could not be molded due to the high viscosity.
CE: s Combined Epoxy Component, measured as meq/kg of semi-aromatic polyester resin, e.g. PBT, PET or PTT. See, supra, Equation 2 and accompanying text. Each Table lists the semi-aromatic polyester resin used.
MV-5 is Initial Melt Viscosity.
"MV-X=%-age MV-5" is the measured Melt Viscosity at X minutes after heating and equals the Percentage of Initial Melt Viscosity. This variable measures Melt Viscosity Stability.
TS: Tensile Strength.
%-age Retained TS: percentage of tensile strength of exposed test bars relative to tensile strength of unexposed test bars. %-age Retained TS measures Hydrolysis Resistance.

Throughout the results, melt viscosity stability is defined as the property recited in the claims, that is, a composition having each subsequent melt viscosity that is not greater than 160% of its initial melt viscosity is defined as melt stable.

Similarly, when the results show that a composition has at least 60 percent retained Tensile Strength, that composition is defined as hydrolysis resistant.

Table 1 lists PBT to which $Ca_5(PO_4)_3OH$ and/or two different kinds of epoxy components, MF Epoxy A or MF Epoxy B, may be added. C1, C2 and C3 contained no epoxy component. C2 and C3 did contain hydroxyapatite and show that, when there is no epoxy component, adding hydroxyapatite had no effect on melt viscosity stability. C4 shows that adding an epoxy component without hydroxyapatite gave very poor melt viscosity stability. By contrast, E1 and E2 show that adding hydroxyapatite to C4 resulted in a melt stabilized composition that also had good hydrolysis resistance. This table shows that it is the combination of hydroxyapatite with the epoxy component that achieved the claimed, combined result.

Table 2 lists PBT comparative compositions containing both epoxy components, MF Epoxy A and MF Epoxy B, and one of the following components tested as the melt viscosity stabilizer: $Ca_3(PO_4)_2$, $CaHPO_4$, $CaSO_4$, $Na_3PO_4$, Hydrotalcite.

C5 and C6 with $Ca_3(PO_4)_2$ did not exhibit melt viscosity stability. Neither did C10 and C11 with 0.5 wt % $Na_3PO_4$ and hydrotalcite, respectively nor did they exhibit the claimed tensile strength retention. C7 and C9 with $CaHPO_4$ and $CaSO_4$ did exhibit melt viscosity stability only up to about 32 minutes after heating. But confer with Table 4, in which C17 to C20—also with $CaHPO_4$ and $CaSO_4$—were not melt stabilized at 63 minutes after heating.

Table 3 lists compositions comprising two different epoxy components. The comparative compositions substituted one of the following as a melt viscosity stabilizer for hydroxyapatite: $Ca(H_2PO_4)_2$, $NaH_2PO_4$, $Ca_2O_7P_2$. C12, C15 and C16 did not exhibit melt viscosity stability. C13 and C14 did not exhibit hydrolysis resistance. E3, the same composition as C16 except that hydroxyapatite is the melt stabilizer, exhibited the claimed melt viscosity stability and hydrolysis resistance.

Table 4 lists comparative compositions containing either 1.0 or 2.0 wt % of the following calcium or phosphorus containing compounds tested as melt viscosity substitutes for hydroxyapatite: $CaHPO_4$, $CaSO_4$, and $Na_3HP_2O_7$. C17 to C22 shows that each of these compounds was ineffective as a melt viscosity stabilizer. $CaHPO_4$ at 1.0 wt % did not stabilize C17. $Na_3HP_2O_7$ did not give C21 and C22 both melt viscosity stability and hydrolysis resistance.

Table 5 lists comparative compositions, C23 to C28, containing the following compounds tested as melt viscosity substitutes for hydroxyapatite: $Ca_3(PO_4)_2$, $Na_2HPO_4$, Calcium Stearate and Barium Sulfate. None of these exhibited the claimed, combined property of melt viscosity stability and hydrolysis resistance.

TABLE 1

|  | C1 | C2 | C3 | C4 | E1 | E2 |
|---|---|---|---|---|---|---|
| MATERIAL |  |  |  |  |  |  |
| Glass Fiber A | 30 | 30 | 30 | 30 | 30 | 30 |
| PBT | 69.2 | 68.2 | 67.2 | 60.7 | 59.7 | 58.7 |
| Antioxidant | 0.3 | 0.3 | 0.3 | 0.3 | 0.3 | 0.3 |
| Lubricant | 0.5 | 0.5 | 0.5 | 0.5 | 0.5 | 0.5 |
| Toughener | 0 | 0 | 0 | 6.5 | 6.5 | 6.5 |
| MF Epoxy A | 0 | 0 | 0 | 1.6 | 1.6 | 1.6 |
| MF Epoxy B | 0 | 0 | 0 | 0.4 | 0.4 | 0.4 |
| $Ca_5(PO_4)_3OH$ | 0 | 1.0 | 2.0 | 0 | 1.0 | 2.0 |
| PHYSICAL PROPERTY |  |  |  |  |  |  |
| CE, meq/kg PBT | 0 | 0 | 0 | 110 | 112 | 114 |
| MV-5 | 157 | 169 | 167 | 160 | 158 | 170 |
| MV-10 = %-age MV-5 | 131 = 83 | 142 = 84 | 147 = 88 | 147 = 92 | 143 = 91 | 164 = 96 |
| MV-16 = %-age MV-5 | 112 = 71 | 124 = 73 | 131 = 78 | 168 = 105 | 140 = 89 | 154 = 91 |
| MV-21 = %-age MV-5 | 101 = 64 | 109 = 64 | 123 = 74 | 224 = 140 | 126 = 80 | 117 = 69 |
| MV-26 = %-age MV-5 | 91 = 58 | 94 = 56 | 105 = 63 | 352 = 220 | 128 = 81 | 114 = 67 |
| MV-32 = %-age MV-5 | 84 = 54 | 86 = 51 | 92 = 55 | 498 = 311 | 136 = 86 | 109 = 64 |
| MV-39 = %-age MV-5 | 75 = 48 | 82 = 49 | 81 = 49 | 585 = 366 | 142 = 90 | 106 = 62 |
| MV-43 = %-age MV-5 | 69 = 44 | 66 = 39 | 76 = 46 | 657 = 411 | 152 = 96 | 103 = 61 |
| MV-48 = %-age MV-5 | 65 = 41 | 67 = 40 | 73 = 44 | 685 = 428 | 166 = 105 | 102 = 60 |
| MV-53 = %-age MV-5 | 58 = 37 | 59 = 35 | 62 = 37 | NM | 183 = 116 | 98 = 58 |
| MV-59 = %-age MV-5 | 55 = 35 | 65 = 38 | 58 = 35 | NM | 203 = 128 | 95 = 56 |
| MV-63 = %-age MV-5 | 49 = 31 | 52 = 31 | 55 = 33 | NM | NM | 99 = 58 |
| TS (MPa) @ 0 hr | 143 | 135 | 127 | 129 | 129 | 127 |
| TS-1 (MPa) @ 150 hr | 42 | 38 | 36 | 106.7 | 109 | 111 |
| %-age Retained TS-1 | 29 | 28 | 29 | 82 | 85 | 87 |
| TS-2 (MPa) @ 100 hr | NM | 33 | 31 | 106 | 111 | NM |
| %-age Retained TS-2 | NM | 25 | 24 | 81 | 86 | NM |

NM—not measured; insufficient sample

TABLE 2

|  | C5 | C6 | C7 | C8 | C9 | C10 | C11 |
|---|---|---|---|---|---|---|---|
| MATERIAL |  |  |  |  |  |  |  |
| Glass Fiber A | 30 | 30 | 30 | 30 | 30 | 30 | 30 |
| PBT | 59.7 | 58.7 | 59.7 | 58.7 | 59.7 | 60.2 | 60.2 |
| Antioxidant | 0.3 | 0.3 | 0.3 | 0.3 | 0.3 | 0.3 | 0.3 |
| Lubricant | 0.5 | 0.5 | 0.5 | 0.5 | 0.5 | 0.5 | 0.5 |
| Toughener | 6.5 | 6.5 | 6.5 | 6.5 | 6.5 | 6.5 | 6.5 |
| MF Epoxy A | 1.6 | 1.6 | 1.6 | 1.6 | 1.6 | 1.6 | 1.6 |
| MF Epoxy B | 0.4 | 0.4 | 0.4 | 0.4 | 0.4 | 0.4 | 0.4 |
| $Ca_3(PO_4)_2$ | 1 | 2 | 0 | 0 | 0 | 0 | 0 |
| $CaHPO_4$ | 0 | 0 | 1 | 2 | 0 | 0 | 0 |
| $CaSO_4$ | 0 | 0 | 0 | 0 | 1 | 0 | 0 |
| $Na_3PO_4$ | 0 | 0 | 0 | 0 | 0 | 0.5 | 0 |
| Hydrotalcite | 0 | 0 | 0 | 0 | 0 | 0 | 0.5 |
| PHYSICAL PROPERTY |  |  |  |  |  |  |  |
| CE, meq/kg PBT | 112 | 114 | 112 | 114 | 112 | 111 | 112 |
| MV-5 | 156 | 163 | 159 | 160 | 157 | 308 | 115 |
| MV-10 = %-age MV-5 | 145 = 93 | 156 = 96 | 145 = 91 | 145 = 91 | 138 = 88 | 495 = 161 | 104 = 90 |
| MV-16 = %-age MV-5 | 149 = 96 | 175 = 107 | 138 = 87 | 140 = 88 | 128 = 82 | 563 = 183 | 100 = 87 |
| MV-21 = %-age MV-5 | 170 = 109 | 263 = 161 | 146 = 92 | 140 = 88 | 131 = 83 | 487 = 158 | 122 = 106 |
| MV-26 = %-age MV-5 | 232 = 149 | 515 = 316 | 155 = 97 | 142 = 89 | 139 = 89 | 569 = 185 | 205 = 178 |
| MV-32 = %-age MV-5 | 387 = 248 | 779 = 478 | 176 = 111 | 142 = 89 | 150 = 96 | 674 = 219 | 260 = 226 |
| MV-39 = %-age MV-5 | 571 = 366 | 905 = 555 | 221 = 139 | 151 = 94 | 106 = 102 | 773 = 251 | 311 = 270 |
| MV-43 = %-age MV-5 | 711 = 456 | 964 = 591 | 296 = 186 | 159 = 99 | 179 = 114 | 865 = 281 | 306 = 266 |

TABLE 2-continued

|  | C5 | C6 | C7 | C8 | C9 | C10 | C11 |
|---|---|---|---|---|---|---|---|
| MV-48 = %-age MV-5 | 762 = 488 | 979 = 601 | 395 = 248 | 174 = 109 | 207 = 132 | 863 = 280 | 303 = 236 |
| MV-53 = %-age MV-5 | 782 = 501 | 956 = 587 | 437 = 275 | 189 = 118 | 292 = 186 | 814 = 264 | 231 = 201 |
| MV-59 = %-age MV-5 | NM | 907 = 556 | 437 = 275 | 204 = 128 | 375 = 239 | 750 = 244 | 177 = 154 |
| MV-63 = %-age MV-5 | NM | NM | 421 = 265 | 228 = 143 | 410 = 261 | 698 = 227 | 116 = 101 |
| TS (MPa) @ 0 hr | 122 | 117 | 127 | 127 | 127 | 130 | 129 |
| TS-1 (MPa) @ 150 hr | 102.8 | 98.5 | 107.9 | 107.9 | 106.9 | 44.8 | 69.6 |
| %-age Retained TS-1 | 84 | 84 | 85 | 85 | 84 | 35 | 54 |
| TS-2 (MPa) @ 100 hr | 103 | 100 | 110 | 110 | 109 | 40 | 68 |
| %-age Retained TS-2 | 84 | 84 | 86 | 86 | 85 | 30 | 53 |

TABLE 3

|  | C12 | C13 | C14 | C15 | C16 | E3 |
|---|---|---|---|---|---|---|
| MATERIAL |  |  |  |  |  |  |
| Glass Fiber A | 30 | 30 | 30 | 30 | 30 | 30 |
| PBT | 60.7 | 60.2 | 60.2 | 59.7 | 58.7 | 59.7 |
| Antioxidant | 0.3 | 0.3 | 0.3 | 0.3 | 0.3 | 0.3 |
| Lubricant | 0.5 | 0.5 | 0.5 | 0.5 | 0.5 | 0.5 |
| Toughener | 6.5 | 6.5 | 6.5 | 6.5 | 6.5 | 6.5 |
| MF Epoxy A | 1.6 | 1.6 | 1.6 | 1.6 | 1.6 | 1.6 |
| MF Epoxy B | 0.4 | 0.4 | 0.4 | 0.4 | 0.4 | 0.4 |
| $Ca_5(PO_4)_3OH$ | 0 | 0 | 0 | 0 | 0 | 1.0 |
| $Ca(H_2PO_4)_2$ | 0 | 0.5 | 0 | 0 | 0 | 0 |
| $NaH_2PO_4$ | 0 | 0 | 0.5 | 0 | 0 | 0 |
| $Ca_2O_7P_2$ | 0 | 0 | 0 | 1.0 | 2.0 | 0 |
| PHYSICAL PROPERTY |  |  |  |  |  |  |
| CE, meq/kg PBT | 110 | 111 | 111 | 112 | 114 | 112 |
| MV-5 | 177 | 225 | 202 | 175 | 169 | 188 |
| MV-10 = %-age MV-5 | 184 = 104 | 212 = 94 | 202 = 100 | 164 = 94 | 167 = 99 | 175 = 93 |
| MV-16 = %-age MV-5 | 194 = 110 | 202 = 90 | 191 = 95 | 166 = 95 | 195 = 115 | 180 = 96 |
| MV-21 = %-age MV-5 | 212 = 120 | 198 = 88 | 188 = 93 | 171 = 98 | 247 = 146 | 184 = 98 |
| MV-26 = %-age MV-5 | 234 = 132 | 184 = 82 | 188 = 93 | 180 = 103 | 350 = 207 | 192 = 102 |
| MV-32 = %-age MV-5 | 266 = 150 | 179 = 80 | 189 = 94 | 196 = 112 | 505 = 299 | 200 = 106 |
| MV-39 = %-age MV-5 | 296 = 167 | 169 = 75 | 181 = 90 | 232 = 133 | 609 = 360 | 208 = 111 |
| MV-43 = %-age MV-5 | 347 = 196 | 153 = 68 | 172 = 85 | 259 = 148 | 671 = 397 | 221 = 118 |
| MV-48 = %-age MV-5 | 391 = 221 | 139 = 62 | 164 = 81 | 325 = 186 | 704 = 417 | 231 = 123 |
| MV-53 = %-age MV-5 | 419 = 237 | 125 = 56 | 154 = 76 | 351 = 201 | 733 = 434 | 244 = 130 |
| MV-59 = %-age MV-5 | 461 = 260 | 120 = 53 | 138 = 68 | 326 = 186 | 751 = 444 | 251 = 134 |
| MV-63 = %-age MV-5 | 464 = 262 | 112 = 50 | 127 = 62 | 356 = 203 | 736 = 436 | 260 = 138 |
| TS (MPa) @ 0 hr | 133 | 127 | 127 | 128 | 127 | 132 |
| TS-1 (MPa) @ 150 hr | 101 | 31 | 50 | 102 | 103 | 107 |
| %-age Retained TS-1 | 76 | 24 | 39 | 79 | 81 | 81 |
| TS-2 (MPa) @ 100 hr | 114 | 48 | 67 | 103 | 107 | 122 |
| %-age Retained TS-2 | 86 | 38 | 53 | 81 | 84 | 92 |

TABLE 4

|  | C17 | C18 | C19 | C20 | C21 | C22 |
|---|---|---|---|---|---|---|
| MATERIAL |  |  |  |  |  |  |
| Glass Fiber A | 30 | 30 | 30 | 30 | 30 | 30 |
| PBT | 59.7 | 58.7 | 59.7 | 58.7 | 59.7 | 58.7 |
| Antioxidant | 0.3 | 0.3 | 0.3 | 0.3 | 0.3 | 0.3 |
| Lubricant | 0.5 | 0.5 | 0.5 | 0.5 | 0.5 | 0.5 |
| Toughener | 6.5 | 6.5 | 6.5 | 6.5 | 6.5 | 6.5 |
| MF Epoxy A | 1.6 | 1.6 | 1.6 | 1.6 | 1.6 | 1.6 |
| MF Epoxy B | 0.4 | 0.4 | 0.4 | 0.4 | 0.4 | 0.4 |
| $CaHPO_4$ | 1.0 | 2.0 | 0 | 0 | 0 | 0 |
| $CaSO_4$ | 0 | 0 | 1.0 | 2.0 | 0 | 0 |
| $Na_3HP_2O_7$ | 0 | 0 | 0 | 0 | 1.0 | 2.0 |
| PHYSICAL PROPERTY |  |  |  |  |  |  |
| CE, meq/kg PBT | 112 | 114 | 112 | 114 | 112 | 114 |
| MV-5 | 165 | 172 | 174 | 165 | 182 | 188 |
| MV-10 = %-age MV-5 | 148 = 90 | 148 = 86 | 162 = 93 | 155 = 94 | 165 = 91 | 176 = 94 |
| MV-16 = %-age MV-5 | 157 = 95 | 137 = 80 | 167 = 96 | 156 = 95 | 152 = 84 | 165 = 88 |
| MV-21 = %-age MV-5 | 166 = 101 | 146 = 85 | 177 = 102 | 175 = 106 | 142 = 78 | 157 = 84 |
| MV-26 = %-age MV-5 | 182 = 110 | 156 = 91 | 200 = 115 | 204 = 124 | 149 = 82 | 150 = 80 |
| MV-32 = %-age MV-5 | 215 = 130 | 171 = 99 | 225 = 129 | 217 = 132 | 143 = 79 | 143 = 76 |

TABLE 4-continued

|  | C17 | C18 | C19 | C20 | C21 | C22 |
|---|---|---|---|---|---|---|
| MV-39 = %-age MV-5 | 255 = 155 | 186 = 108 | 245 = 141 | 250 = 152 | 144 = 79 | 138 = 73 |
| MV-43 = %-age MV-5 | 326 = 198 | 207 = 120 | 275 = 158 | 302 = 183 | 139 = 76 | 135 = 72 |
| MV-48 = %-age MV-5 | 402 = 244 | 222 = 129 | 312 = 179 | 323 = 196 | 133 = 73 | 130 = 69 |
| MV-53 = %-age MV-5 | 445 = 270 | 271 = 158 | 319 = 183 | 362 = 219 | 140 = 77 | 129 = 69 |
| MV-59 = %-age MV-5 | 472 = 286 | 303 = 176 | 287 = 165 | 377 = 228 | 134 = 74 | 126 = 67 |
| MV-63 = %-age MV-5 | 478 = 290 | 354 = 206 | 300 = 172 | 375 = 227 | 139 = 76 | 123 = 65 |
| TS (MPa) @ 0 hr | 133 | 131 | 134 | 135 | 131 | 132 |
| TS-1 (MPa) @ 150 hr | 107 | 106 | 107 | 107 | 57 | 52 |
| %-age Retained TS-1 | 81 | 81 | 80 | 79 | 44 | 39 |
| TS-2 (MPa) @ 100 hr | 111 | 109 | 108 | 111 | 68 | 61 |
| %-age Retained TS-2 | 84 | 83 | 81 | 82 | 52 | 46 |

TABLE 5

|  | C23 | C24 | C25 | C26 | 27C | C28 |
|---|---|---|---|---|---|---|
| MATERIAL | | | | | | |
| Glass Fiber A | 30 | 30 | 30 | 30 | 30 | 30 |
| PBT | 59.7 | 58.7 | 59.7 | 58.7 | 59.7 | 59.7 |
| Antioxidant | 0.3 | 0.3 | 0.3 | 0.3 | 0.3 | 0.3 |
| Lubricant | 0.5 | 0.5 | 0.5 | 0.5 | 0.5 | 0.5 |
| Toughener | 6.5 | 6.5 | 6.5 | 6.5 | 6.5 | 6.5 |
| MF Epoxy A | 1.6 | 1.6 | 1.6 | 1.6 | 1.6 | 1.6 |
| MF Epoxy B | 0.4 | 0.4 | 0.4 | 0.4 | 0.4 | 0.4 |
| $Ca_3(PO_4)_2$ | 1.0 | 2.0 | 0 | 0 | 0 | 0 |
| $Na_2HPO_4$ | 0 | 0 | 1.0 | 2.0 | 0 | 0 |
| Calcium Stearate | 0 | 0 | 0 | 0 | 1.0 | 0 |
| Barium Sulfate | 0 | 0 | 0 | 0 | 0 | 1.0 |
| PHYSICAL PROPERTY | | | | | | |
| CE, meq/kg PBT | 112 | 114 | 112 | 114 | 112 | 112 |
| MV-5 | 170 | 177 | 142 | 159 | 393 | 212 |
| MV-10 = %-age MV-5 | 273 = 161 | 664 = 375 | 133 = 94 | 140 = 88 | 507 = 129 | 280 = 132 |
| MV-16 = %-age MV-5 | 583 = 343 | 917 = 518 | 136 = 96 | 138 = 87 | 574 = 146 | 677 = 319 |
| MV-21 = %-age MV-5 | 729 = 429 | 982 = 555 | 140 = 99 | 126 = 79 | 646 = 164 | 884 = 417 |
| MV-26 = %-age MV-5 | 782 = 460 | 958 = 541 | 143 = 101 | 110 = 69 | 718 = 183 | 988 = 466 |
| MV-32 = %-age MV-5 | 749 = 441 | 918 = 519 | 145 = 102 | 105 = 66 | 731 = 186 | 1038 = 490 |
| MV-39 = %-age MV-5 | 680 = 400 | 855 = 483 | 132 = 93 | 88 = 55 | 725 = 184 | 1027 = 484 |
| MV-43 = %-age MV-5 | 615 = 362 | 770 = 435 | 109 = 77 | 72 = 45 | 675 = 172 | 991 = 467 |
| MV-48 = %-age MV-5 | 540 = 318 | 685 = 387 | 101 = 71 | 63 = 40 | 638 = 162 | NM |
| MV-53 = %-age MV-5 | 487 = 286 | 637 = 360 | 87 = 61 | 49 = 31 | 613 = 156 | NM |
| MV-59 = %-age MV-5 | 430 = 253 | 565 = 319 | 77 = 54 | 48 = 30 | NM | NM |
| MV-63 = %-age MV-5 | 394 = 232 | 491 = 277 | 62 = 44 | 44 = 28 | NM | NM |
| TS (MPa) @ 0 hr | 127 | 124 | 130 | 129 | 131 | 130 |
| TS-1 (MPa) @ 150 hr | 100 | 98 | 48 | 40 | 41 | 88 |
| %-age Retained TS-1 | 79 | 79 | 37 | 31 | 32 | 68 |
| TS-2 (MPa) @ 100 hr | 92 | 100 | 57 | 52 | 57 | 99 |
| %-age Retained TS-2 | 72 | 81 | 44 | 40 | 43 | 76 |

Table 6 lists compositions that had substantially the same components in the same amounts. C29 had a different glass fiber and E4 and E5 contained 1 wt % and 2 wt % hydroxyapatite, respectively. Only E4 and E5 exhibited the claimed melt viscosity stability and hydrolysis resistance. This table, along with Table 1, highlights that the claimed amount of hydroxyapatite with the claimed epoxy component was responsible for the claimed, combined property of melt viscosity stability plus hydrolysis resistance.

Tables 6 and 7 show that the Comparative Tracking Index (CTI) of articles containing compositions having 0.5 wt % or greater hydroxyapatite was greater than 400.

Table 7 shows how hydroxyapatite amount affected the melt viscosity stability and the hydrolysis resistance. E6 and E10 contained 0.5 wt % hydroxyapatite; the melt viscosity of both examples was stabilized up to about 48 minutes after heating. Beyond 48 minutes after heating, the hydroxyapatite appears to have been depleted, which accounted for the melt viscosity increase of E6 and E10. With amounts of 0.75 wt % to 3 wt % hydroxyapatite, E7 to E9 and E11 exhibited melt viscosity stability even at 63 minutes after heating. Relative to C31 without hydroxyapatite, E6 and E7 show that the CTI increased as hydroxyapatite increased.

Table 8 lists examples in which the semi-aromatic polyester resin was PTT. C34 and C35 show, when the epoxy functionality was greater than about 40 meq/kg PTT resin, the melt viscosity exhibited a considerable increase, especially when compared to C33, the same composition but lacking epoxy functionality.

TABLE 6

|  | C29 | C30 | E4 | E5 |
|---|---|---|---|---|
| MATERIAL | | | | |
| Glass Fiber B | 15 | 0 | 0 | 0 |
| Glass Fiber A | 0 | 15 | 15 | 15 |
| PBT | 75 | 75 | 74 | 73 |
| Antioxidant | 0.3 | 0.3 | 0.3 | 0.3 |

TABLE 6-continued

|  | C29 | C30 | E4 | E5 |
|---|---|---|---|---|
| Lubricant | 0.5 | 0.5 | 0.5 | 0.5 |
| Toughener | 6.0 | 6.0 | 6.0 | 6.0 |
| MF Epoxy A | 1.9 | 1.9 | 1.9 | 1.9 |
| MF Epoxy B | 0.4 | 0.4 | 0.4 | 0.4 |
| Plasticizer | 0.9 | 0.9 | 0.9 | 0.9 |
| $Ca_5(PO_4)_3OH$ | 0 | 0 | 1 | 2 |
| PHYSICAL PROPERTY | | | | |
| CE, meq/kg PBT | 94 | 94 | 95 | 96 |
| MV-5 | 112 | 114 | 148 | 137 |
| MV-10 = %-age MV-5 | 119 = 106 | 117 = 103 | 129 = 87 | 123 = 90 |
| MV-16 = %-age MV-5 | 143 = 128 | 130 = 114 | 118 = 80 | 110 = 80 |
| MV-21 = %-age MV-5 | 211 = 188 | 153 = 134 | 112 = 76 | 101 = 74 |
| MV-26 = %-age MV-5 | 295 = 263 | 180 = 158 | 110 = 74 | 96 = 70 |
| MV-32 = %-age MV-5 | 429 = 383 | 214 = 188 | 114 = 77 | 98 = 72 |
| MV-39 = %-age MV-5 | 515 = 460 | 271 = 238 | 119 = 80 | 92 = 67 |
| MV-43 = %-age MV-5 | 553 = 494 | 296 = 260 | 125 = 84 | 94 = 69 |
| MV-48 = %-age MV-5 | 574 = 513 | 324 = 284 | 130 = 88 | 97 = 71 |
| MV-53 = %-age MV-5 | 562 = 502 | 346 = 304 | 136 = 92 | 93 = 68 |
| MV-59 = %-age MV-5 | 529 = 472 | 341 = 299 | 136 = 92 | 99 = 72 |
| MV-63 = %-age MV-5 | NM | 339 = 297 | 134 = 91 | 90 = 66 |
| TS (MPa) 0 hr | 88 | 93 | 94 | 93 |
| TS-1 (MPa) 150 hr | 82 | 78 | 75 | 75 |
| %-age Retained TS-1 | 93 | 83 | 80 | 81 |
| TS-2 (MPa) 100 hr | 82 | 75 | 71 | 72 |
| %-age Retained TS-2 | 93 | 80 | 76 | 77 |
| CTI | 350 | 375 | 600 | 600 |

TABLE 7

|  | C31 | E6 | E7 | E8 | E9 | C32 | E10 | E11 |
|---|---|---|---|---|---|---|---|---|
| Material | | | | | | | | |
| Glass Fiber B | 15 | 15 | 15 | 15 | 15 | 0 | 0 | 0 |
| Glass Fiber A | 0 | 0 | 0 | 0 | 0 | 15 | 15 | 15 |
| PBT | 75 | 74.5 | 74 | 73 | 72.5 | 75 | 74.5 | 74 |
| Antioxidant | 0.3 | 0.3 | 0.3 | 0.3 | 0.3 | 0.3 | 0.3 | 0.3 |
| Lubricant | 0.5 | 0.5 | 0.5 | 0.5 | 0.5 | 0.5 | 0.5 | 0.5 |
| Toughener | 6.0 | 6.0 | 6.0 | 6.0 | 6.0 | 6.0 | 6.0 | 6.0 |
| MF Epoxy B | 1.9 | 1.9 | 1.9 | 1.9 | 1.9 | 1.9 | 1.9 | 1.9 |
| MF Epoxy C | 0.4 | 0.4 | 0.4 | 0.4 | 0.4 | 0.4 | 0.4 | 0.4 |
| $Ca_5(PO_4)_3OH$ | 0 | 0.5 | 1.0 | 2.0 | 2.5 | 0 | 0.5 | 1.0 |
| Plasticizer | 0.9 | 0.9 | 0.9 | 0.9 | 0.9 | 0.9 | 0.9 | 0.9 |
| PHYSICAL PROPERTY | | | | | | | | |
| CE, meq/kg PBT | 94 | 94 | 95 | 96 | 97 | 94 | 94 | 95 |
| MV-5 | 102 | 114 | 115 | 130 | 140 | 110 | 117 | 119 |
| MV-11 = -% age MV-5 | 123/121 | 106/93 | 107/93 | 114/88 | 124/89 | 111/101 | 109/93 | 105/88 |
| MV-16 = %-age MV-5 | 186/182 | 110/96 | 99/86 | 103/79 | 112/80 | 120/109 | 108/92 | 101/85 |
| MV-21 = %-age MV-5 | 302/296 | 116/102 | 99/86 | 94/72 | 111/79 | 136/124 | 116/99 | 101/85 |
| MV-27 = %-age MV-5 | 422/414 | 132/116 | 111/97 | 92/71 | 95/68 | 153/139 | 126/108 | 100/84 |
| MV-32 = %-age MV-5 | 537/526 | 139/122 | 118/103 | 85/65 | 93/66 | 183/166 | 122/104 | 111/93 |
| MV-37 = %-age MV-5 | 597/585 | 138/121 | 122/106 | 88/68 | 87/62 | 189/172 | 135/115 | 120/101 |
| MV-42 = %-age MV-5 | 629/617 | 158/139 | 130/113 | 89/68 | 83/59 | 235/214 | 160/137 | 123/103 |
| MV-48 = %-age MV-5 | 660/647 | 165/145 | 137/119 | 91/70 | 86/61 | 267/243 | 174/149 | 135/113 |
| MV-53 = %-age MV-5 | 668/655 | 180/158 | 144/125 | 87/67 | 88/63 | 281/255 | 199/170 | 134/113 |
| MV-59 = %-age MV-5 | 651/638 | 194/170 | 162/141 | 86/66 | 85/61 | 308/280 | 218/186 | 135/113 |
| MV-63 = %-age MV-5 | NM | 211/185 | 170/148 | 89/68 | 82/59 | 312/284 | 248/212 | 141/118 |
| TS (MPa) @ 0 hr | 94 | 93 | 93 | 92 | 92 | 97 | 97 | 97 |
| TS-1 (MPa) @ 150 hr | 80 | 68 | 70 | 68 | 67 | 74 | 73 | 72 |
| %-age Retained TS-1 | 85 | 74 | 75 | 74 | 73 | 76 | 75 | 75 |
| TS-2 (MPa) @ 100 hr | NM | NM | NM | 64 | 63 | 70 | 70 | 69 |
| %-age Retained TS-2 | NM | NM | NM | 70 | 69 | 72 | 71 | 71 |
| CTI | 350 | 450 | 550 | NT | NT | NT | NT | NT |

NM—not measured; insufficient sample

TABLE 8

|  | C33 | C34 | C35 | E12 | E13 |
|---|---|---|---|---|---|
| MATERIAL | | | | | |
| Glass Fiber A | 30 | 30 | 30 | 30 | 30 |
| PTT | 68.9 | 66.9 | 65.9 | 65.4 | 64.4 |
| Antioxidant | 0.1 | 0.1 | 0.1 | 0.1 | 0.1 |
| Lubricant | 0.5 | 0.5 | 0.5 | 0.5 | 0.5 |
| MF Epoxy A | 0 | 2 | 3 | 2 | 3 |
| $Ca_5(PO_4)_3OH$ | 0 | 0 | 0 | 1.5 | 1.5 |
| Talc | 0.5 | 0.5 | 0.5 | 0.5 | 0.5 |
| PHYSICAL PROPERTY | | | | | |
| CE, meq/kg PTT | 0 | 46 | 70 | 47 | 72 |
| MV-5 | 178 | 159 | 129 | 156 | 163 |
| MV-10 = %-age MV-5 | 136/76 | 114/72 | 225/174 | 125/80 | 110/67 |
| MV-16 = %-age MV-5 | 110/62 | 104/65 | 529/410 | 114/73 | 84/52 |
| MV-21 = %-age MV-5 | 96/54 | 110/69 | 698/541 | 105/67 | 76/47 |
| MV-26 = %-age MV-5 | 87/49 | 198/125 | 798/619 | 100/64 | 71/44 |
| MV-32 = %-age MV-5 | 79/44 | 280/176 | 853/661 | 93/60 | 72/44 |
| MV-39 = %-age MV-5 | 70/39 | 381/240 | 879/681 | 91/58 | 70/43 |
| MV-43 = %-age MV-5 | 65/37 | 451/284 | 878/681 | 100/64 | 70/43 |
| MV-48 = %-age MV-5 | 60/34 | 463/291 | 880/682 | 110/71 | 71/44 |
| MV-53 = %-age MV-5 | 55/31 | 459/289 | 870/674 | 113/72 | 76/47 |
| MV-59 = %-age MV-5 | 50/28 | 432/272 | 805/624 | 129/83 | 91/56 |
| MV-63 = %-age MV-5 | 44/25 | 382/240 | NM | 140/90 | 113/69 |
| TS (MPa) @ 0 hr | 146 | 150 | 156 | 157 | 156 |
| TS-1 (MPa) @ 100 hr | 68 | 107 | 107 | 113 | 113 |

TABLE 8-continued

|  | C33 | C34 | C35 | E12 | E13 |
|---|---|---|---|---|---|
| %-age Retained TS-1 | 46 | 71 | 69 | 72 | 72 |
| TS-2 (MPa) @ 50 hr | 80 | 116 | 112 | 126 | 124 |
| %-age Retained TS-2 | 54 | 77 | 71 | 81 | 79 |

In Table 9, C36 to C43 show the effect of the absence of glass fibers. C36 to C39 lacked hydroxyapatite but contained a multi-functional effect epoxy compound. C37 to C39 had an epoxy component greater than 40 meq/kg polyester resin but lacked reinforcing agents, e.g., glass fibers or flakes, and exhibited melt viscosity stability but had very poor tensile strength retention.

C40, containing sodium tetraborate, a basic compound at about 9.5 pH, exhibited an unstable initial melt viscosity of 356, showing that effect of such strongly basic compounds on initial melt viscosity instability. Adding hydroxyapatite to compositions having sodium tetraborate slightly reduced the initial melt viscosity instability; but, the MV-5 value of 295 was still undesirable. C40 and C43 showed rapid viscosity increase during melt extrusion to form pellets/granules.

Lacking glass fibers or flakes, C41 to C43 exhibited poor tensile strength retention after 100 hours, even though both contained a multi-functional epoxy compound and hydroxyapatite. There was insufficient sample material available to evaluate under TS-2 conditions.

In Table 10, C46 to C47 had combined epoxy functionality of greater than about 40 meq/kg polyester resin but lacked hydroxyapatite and exhibited poor melt viscosity stability. E14 to E17 shows that adding hydroxyapatite greatly improved melt viscosity stability and simultaneously improved hydrolysis resistance. It is important to note that at a combined epoxy milliequivalents of less than 40 meq/kg PBT, the subsequent melt viscosity did not increase to more than 134% of the initial melt viscosity. The addition of a melt viscosity stabilizer in PBT compositions having a combined epoxy component of less than 40 meq/kg PBT is deduced to be unnecessary.

The compositions in Table 11 were similar to those in Table 10, except added Fyrolflex® RDP-LT. C48 to C54 in Table 11 demonstrate that resorcinol bis(diphenyl phosphate) flame retardant, such as Fyrolflex® RDP-LT, greatly reduced hydrolysis resistance, regardless of whether the polyester composition contained an epoxy component and/or hydroxyapatite as evidenced by extremely low tensile strengths.

TABLE 9

|  | C36 | C37 | C38 | C39 | C40 | C41 | C42 | C43 |
|---|---|---|---|---|---|---|---|---|
| MATERIAL |  |  |  |  |  |  |  |  |
| PBT | 99.4 | 96.4 | 95.9 | 95.4 | 96.2 | 94.9 | 94.4 | 94.7 |
| Antioxidant | 0.1 | 0.1 | 0.1 | 0.1 | 0.1 | 0.1 | 0.1 | 0.1 |
| Lubricant | 0.5 | 0.5 | 0.5 | 0.5 | 0.5 | 0.5 | 0.5 | 0.5 |
| MF Epoxy A | 0 | 3.0 | 3.0 | 3.0 | 3.0 | 3.0 | 3.0 | 3.0 |
| MF Epoxy B | 0 | 0 | 0.5 | 1 | 0 | 0 | 0.5 | 0 |
| $Ca_5(PO_4)_3OH$ | 0 | 0 | 0 | 0 | 0 | 1.5 | 1.5 | 1.5 |
| sodium tetraborate decahydrate | 0 | 0 | 0 | 0 | 0.2 | 0 | 0 | 0.2 |
| PHYSICAL PROPERTY |  |  |  |  |  |  |  |  |
| CE, meq/kg PBT | 0 | 47 | 73 | 98 | 48 | 47 | 74 | 49 |
| MV-5 | 180 | 145 | 138 | 140 | 356 | 175 | 183 | 295 |
| MV-10 = %-age MV-5 | 133 = 74 | 114 = 79 | 112 = 81 | 106 = 76 | 574 = 161 | 138 = 79 | 142 = 78 | 260 = 88 |
| MV-16 = %-age MV-5 | 112 = 62 | 107 = 73 | 94 = 68 | 89 = 64 | 692 = 194 | 110 = 63 | 115 = 63 | 217 = 74 |
| MV-21 = %-age MV-5 | 96 = 53 | 104 = 72 | 84 = 61 | 79 = 56 | 836 = 235 | 91 = 52 | 97 = 53 | 199 = 67 |
| MV-26 = %-age MV-5 | 82 = 46 | 105 = 72 | 81 = 59 | 72 = 51 | 752=/211 | 77 = 44 | 85 = 46 | 185 = 63 |
| MV-32 = %age MV-5 | 70 = 39 | 110 = 76 | 76 = 55 | 67 = 48 | 605 = 170 | 67 = 38 | 72 = 39 | 177 = 60 |
| MV-39 = %age MV-5 | 61 = 34 | 126 = 87 | 73 = 53 | 61 = 44 | 578 = 162 | 60 = 34 | 59 = 32 | 176 = 60 |
| MV-43 = %age MV-5 | 53 = 29 | 132 = 91 | 73 = 53 | 60 = 43 | NM | 53 = 30 | 57 = 31 | 176 = 60 |
| MV-48 = %age MV-5 | 47 = 26 | 143 = 99 | 74 = 54 | 60 = 43 | NM | 49 = 28 | 53 = 29 | NM |
| MV-53 = %age MV-5 | 40 = 22 | 149 = 103 | 77 = 55 | 60 = 43 | NM | 44 = 25 | 49 = 27 | NM |
| MV-59 = %age MV-5 | 35 = 19 | 143 = 99 | 87 = 63 | 76 = 54 | NM | 40 = 23 | 45 = 25 | NM |
| MV-63 = %age MV-5 | 31 = 18 | 148 = 103 | NM | 80 = 57 | NM | 34 = 19 | 43 = 24 | NM |
| TS (MPa) @ 0 hr | 55 | 56 | 56 | 56 | 55 | 56 | 56 | 55 |
| TS-1 (MPa) @ 50 hr | 15 | 16 | 16 | 16 | 53 | 57 | 56 | 55 |
| TS-1 (MPa) @ 100 hr | 5 | 9 | 8 | 10 | 15 | 11 | 14 | 16 |
| %-age Retained TS-1 @ 50 h | 27 | 28 | 28 | 28 | 97 | 102 | 100 | 99 |
| % age Retained TS-1 @ 100 h | 9 | 17 | 14 | 17 | 27 | 20 | 25 | 28 |

TABLE 10

|  | C44 | C45 | C46 | C47 | E14 | E15 | E16 | E17 |
|---|---|---|---|---|---|---|---|---|
| MATERIAL |  |  |  |  |  |  |  |  |
| Glass Fiber B | 30 | 30 | 30 | 30 | 30 | 30 | 30 | 30 |
| PBT | 69.85 | 69.35 | 68.35 | 67.35 | 67.35 | 66.35 | 66.35 | 65.35 |
| Antioxidant | 0.15 | 0.15 | 0.15 | 0.15 | 0.15 | 0.15 | 0.15 | 0.15 |
| MF Epoxy C | 0 | 0.5 | 1.5 | 2.5 | 1.5 | 2.5 | 1.5 | 2.5 |
| $Ca_5(PO_4)_3OH$ | 0 | 0 | 0 | 0 | 1 | 1 | 2 | 2 |
| PHYSICAL PROPERTY |  |  |  |  |  |  |  |  |
| CE, meq/kg PBT | 0 | 31 | 93 | 158 | 95 | 160 | 96 | 163 |
| MV-5 | 167 | 209 | 264 | 289 | 180 | 182 | 186 | 182 |

TABLE 10-continued

|  | C44 | C45 | C46 | C47 | E14 | E15 | E16 | E17 |
|---|---|---|---|---|---|---|---|---|
| MV-10 = %-age MV-5 | 143 = 86 | 207 = 99 | 376 = 142 | 298 = 103 | 157 = 87 | 162 = 89 | 163 = 88 | 165 = 91 |
| MV-16 = %-age MV-5 | 129 = 77 | 206 = 99 | 630 = 239 | 312 = 108 | 143 = 79 | 149 = 82 | 149 = 80 | 146 = 80 |
| MV-21 = %-age MV-5 | 118 = 71 | 253 = 121 | 729 = 276 | 435 = 151 | 135 = 75 | 141 = 77 | 133 = 72 | 133 = 73 |
| MV-26 = %-age MV-5 | 106 = 63 | 276 = 132 | 966 = 366 | 574 = 199 | 127 = 71 | 136 = 75 | 122 = 66 | 126 = 69 |
| MV-32 = %-age MV-5 | 95 = 57 | 276 = 132 | 1044 = 395 | 789 = 273 | 124 = 69 | 135 = 74 | 115 = 62 | 121 = 66 |
| MV-39 = %-age MV-5 | 87 = 52 | 280 = 134 | 1067 = 404 | 980 = 339 | 124 = 69 | 133 = 73 | 110 = 59 | 114 = 63 |
| MV-43 = %-age MV-5 | 78 = 47 | 259 = 124 | 1054 = 399 | 1178 = 408 | 137 = 76 | 138 = 76 | 107 = 58 | 117 = 64 |
| MV-48 = %-age MV-5 | 72 = 43 | 244 = 117 | 1028 = 389 | 1220 = 422 | 171 = 95 | 154 = 85 | 106 = 57 | 114 = 63 |
| MV-53 = %-age MV-5 | 64 = 38 | 202 = 97 | 1008 = 382 | 1249 = 432 | 169 = 94 | 193 = 106 | 104 = 56 | 112 = 62 |
| MV-59 = %-age MV-5 | 60 = 35 | 178 = 85 | 956 = 362 | 1254 = 434 | 166 = 92 | 204 = 112 | 102 = 55 | 120 = 66 |
| MV-63 = %-age MV-5 | 56 = 33 | 170 = 81 | NM | NM | 175/97 | 255/140 | 101/54 | 128/70 |
| TS (MPa) @ 0 hr | 149 | 148 | 151 | 152 | 149 | 150 | 150 | 150 |
| TS-1 (MPa) @ 150 hr | 43 | 75 | 127 | 108 | 108 | 121 | 131 | 130 |
| % age Retained TS-1 | 29 | 50 | 85 | 72 | 73 | 80 | 87 | 87 |
| TS-2 (MPa) 100 hr | 42 | 73 | 132 | 118 | 104 | 129 | 133 | 135 |
| %-age Retained TS-2 | 28 | 50 | 87 | 78 | 70 | 86 | 89 | 90 |

TABLE 11

|  | C48 | C49 | C50 | C51 | C52 | C53 | C54 |
|---|---|---|---|---|---|---|---|
| MATERIAL |  |  |  |  |  |  |  |
| Glass Fiber | 30 | 30 | 30 | 30 | 30 | 30 | 30 |
| PBT | 56.55 | 56.05 | 54.05 | 55.05 | 53.05 | 54.05 | 52.05 |
| Antioxidant | 0.15 | 0.15 | 0.15 | 0.15 | 0.15 | 0.15 | 0.15 |
| Flame retardant | 13.3 | 13.3 | 13.3 | 13.3 | 13.3 | 13.3 | 13.3 |
| MF Epoxy C | 0 | 0.5 | 2.5 | 0.5 | 2.5 | 0.5 | 2.5 |
| $Ca_5(PO_4)_3OH$ | 0 | 0 | 0 | 1 | 1 | 2 | 2 |
| PHYSICAL PROPERTY |  |  |  |  |  |  |  |
| CE, meq/kg PBT | 0 | 38 | 197 | 39 | 201 | 39 | 204 |
| MV-5 | 88 | 101 | 111 | 88 | 87 | 94 | 91 |
| MV-10 = %-age MV-5 | 77 = 88 | 97 = 96 | 118 = 106 | 79 = 90 | 85 = 98 | 81 = 86 | 84 = 92 |
| MV-16 = %-age MV-5 | 69 = 78 | 93 = 92 | 127 = 114 | 72 = 82 | 87 = 100 | 74 = 79 | 80 = 88 |
| MV-21 = %-age MV-5 | 64 = 73 | 90 = 89 | 142 = 128 | 69 = 78 | 91 = 105 | 68 = 72 | 79 = 87 |
| MV-26 = %-age MV-5 | 57 = 65 | 85 = 85 | 196 = 177 | 65 = 74 | 96 = 110 | 65 = 69 | 82 = 90 |
| MV-32 = %-age MV-5 | 53 = 60 | 86 = 85 | 246 = 222 | 62 = 70 | 108 = 124 | 62 = 66 | 86=/95 |
| MV-39 = %-age MV-5 | 49 = 56 | 82 = 81 | 354 = 319 | 60 = 68 | 148 = 170 | 60 = 64 | 94 = 103 |
| MV-43 = %-age MV-5 | 45 = 51 | 78 = 77 | 468 = 422 | 59 = 67 | 196 = 25 | 63 = 67 | 130 = 143 |
| MV-48 = %-age MV-5 | 44 = 50 | 70 = 69 | 534 = 481 | 59 = 67 | 275 = 316 | 56 = 60 | 172 = 189 |
| MV-53 = %-age MV-5 | 41 = 47 | 67 = 66 | 600 = 541 | 58 = 66 | 346 = 398 | 53 = 56 | 221 = 243 |
| MV-59 = %-age MV-5 | 40 = 45 | 67 = 66 | 643 = 579 | 55 = 63 | 413 = 475 | 50 = 53 | 285 = 313 |
| MV-63 = %-age MV-5 | 34 = 39 | 61 = 60 | 671 = 604 | 55 = 63 | 474 = 545 | 47 = 50 | 333 = 366 |
| TS (MPa) @ 0 hr | 92 | 88 | 85 | 84 | 77 | 82 | 77 |
| TS-1 (MPa) @ 150 hr | 4 | 1 | 2.5 | 2.1 | 3.6 | 1.5 | 4.9 |
| %-age Retained TS-1 | 4 | 1 | 3 | 3 | 5 | 2 | 6 |

Table 12 shows the effect of adding a phosphinate flame retardant (Exolit®) or a melamine cyanurate flame retardant synergist (MELAPUR MC25) on the melt viscosity stability of these compositions. Both are phosphorus/phosphate containing compounds that exhibit pH of 8 or greater or 6 or less. When included in compositions having hydroxyapatite, they prevented achievement of the recited melt viscosity stability. C55 contained neither epoxy component nor hydroxyapatite. C56 contained less than 40 meq/kg polyester resin of epoxy component, whereas C57 contained greater than 40 meq/kg polyester resin of epoxy component. Each subsequent melt viscosity of C57 was greater than 160% of the initial melt viscosity (MV-5) when no hydroxyapatite was present.

Containing greater than 40 meq/kg polyester resin of epoxy component and hydroxyapatite, both C59 and C61 also had a melamine cyanurate flame retardant synergist; their melt viscosity exceeded 160% MV-5, the recited melt viscosity stability. These show adding a melamine cyanurate synergist destabilized the melt viscosity when hydroxyapatite was present.

Both C58 and C60 had hydroxyapatite and less than 40 meq/kg polyester resin of an epoxy component plus a melamine cyanurate flame retardant synergist, which resulted in large initial melt viscosity (MV-5) values and was undesirable as molding these compositions would be difficult.

Both C62 and C63 contained a phosphinate flame retardant. C62 did not contain an epoxy component and exhibited neither a large initial melt viscosity nor an increase in subsequent melt viscosity but had very poor tensile strength. Adding the epoxy component to C63 resulted in a very large MV-5 value, undesirable for molding. C63 could likely not have been molded.

Table 13 shows the destabilizing effect of a resorcinol bis(diphenyl phosphate) flame retardant on the hydrolysis resistance of these compositions. C64 to C73, whether containing hydroxyapatite or not, exhibited extremely poor tensile strength retention. Flame retardants containing phosphate appeared to affect the balancing between the epoxy component, glass fiber, and hydroxyapatite by moving the pH of the composition to outside of 6 and 8, when the molded composition was exposed to heat and humidity.

In Table 14, E18 and E19 exhibited the combined, claimed melt viscosity stability and hydrolysis resistance. C75 was identical to E18, except for hydroxyapatite. C75 did not exhibit melt viscosity stability throughout the period of viscosity measurement, but had clear melt viscosity instability at 26 minutes after heating and beyond. C75 without the hydroxyapatite would not be a good candidate for molding within a half hour of the melt processing.

C78 and C79 contained hydroxyapatite and resorcinol bis(diphenyl phosphate) flame retardant and showed that phosphorus containing compositions have extremely poor hydrolysis resistance evidenced by the low tensile strength values.

In Table 15, the compositions all contained the same amount of glass fiber B: E20 and E21 had hydroxyapatite and exhibited the claimed, combined melt viscosity stability and hydrolysis resistance. C80 had no epoxy and no hydroxyapatite and achieved neither the recited hydrolysis resistance nor the recited melt viscosity stability. C81 and C82 contained a multi-functional epoxy compound and toughener but no hydroxyapatite and achieved the desired hydrolysis resistance but not the recited melt viscosity stability.

TABLE 12

| | C55 | C56 | C57 | C58 | C59 | C60 | C61 | C62 | C63 |
|---|---|---|---|---|---|---|---|---|---|
| MATERIAL | | | | | | | | | |
| Glass Fiber B | 30 | 30 | 30 | 30 | 30 | 30 | 30 | 30 | 30 |
| PBT | 60.85 | 60.35 | 58.35 | 59.35 | 57.35 | 58.35 | 56.35 | 54.85 | 52.35 |
| Antioxidant | 0.15 | 0.15 | 0.15 | 0.15 | 0.15 | 0.15 | 0.15 | 0.15 | 0.15 |
| PTFE | 0.25 | 0.25 | 0.25 | 0.25 | 0.25 | 0.25 | 0.25 | 0 | 0 |
| SAN | 0.25 | 0.25 | 0.25 | 0.25 | 0.25 | 0.25 | 0.25 | 0 | 0 |
| FR Synergist | 8.5 | 8.5 | 8.5 | 8.5 | 8.5 | 8.5 | 8.5 | 0 | 0 |
| Organic phosphinate | 0 | 0 | 0 | 0 | 0 | 0 | 0 | 15 | 15 |
| Epoxy C | 0 | 0.5 | 2.5 | 0.5 | 2.5 | 0.5 | 2.5 | 0 | 2.5 |
| $Ca_5(PO_4)_3OH$ | 0 | 0 | 0 | 1 | 1 | 2 | 2 | 0 | 0 |
| PHYSICAL PROPERTY | | | | | | | | | |
| CE, meq/kg PBT | 0 | 35 | 182 | 36 | 185 | 36 | 189 | 0 | 203 |
| MV-5 | 188 | 251 | 448 | 254 | 376 | 279 | 400 | 178 | 794 |
| MV-10 = %-age MV-5 | 158 = 84 | 227 = 90 | 764 = 171 | 235 = 93 | 558 = 148 | 289 = 104 | 513 = 128 | 159 = 89 | 771 = 97 |
| MV-16 = %-age MV-5 | 136 = 72 | 216 = 86 | 850 = 190 | 221 = 87 | 673 = 179 | 281 = 101 | 702 = 176 | 147 = 83 | 669 = 84 |
| MV-21 = %-age MV-5 | 120 = 64 | 198 = 79 | 917 = 205 | 231 = 91 | 763 = 203 | 327 = 117 | 732 = 183 | 118 = 66 | 615 = 77 |
| MV-26 = %-age MV-5 | 111 = 59 | 186 = 74 | 926 = 207 | 212 = 83 | 807 = 215 | 306 = 110 | 752 = 188 | 106 = 60 | 681 = 86 |
| MV-32 = %-age MV-5 | 101 = 54 | 166 = 54 | 907 = 202 | 188 = 74 | 796 = 212 | 194 = 70 | 678 = 170 | 100 = 56 | 721 = 91 |
| MV-39 = %-age MV-5 | 92 = 49 | 153 = 49 | NM | 178 = 70 | 752 = 200 | 192 = 69 | 674 = 169 | 94 = 53 | 577 = 73 |
| MV-43 = %-age MV-5 | 83 = 44 | 140 = 44 | NM | 144 = 57 | 680/181 | NM | 548 = 137 | 84 = 47 | 656 = 83 |
| MV-48 = %-age MV-5 | 78 = 41 | 125 = 41 | NM | 143 = 56 | 605/161 | NM | 488 = 122 | 77 = 43 | 434 = 55 |
| MV-53 = %-age MV-5 | 68 = 36 | 116 = 46 | NM | 119 = 47 | NM | NM | NM | 73 = 41 | 533 = 67 |
| MV-59 = %-age MV-5 | 68 = 36 | 103 = 41 | NM | 114=/45 | NM | NM | NM | 64 = 36 | 500 = 63 |
| MV-63 = %-age MV-5 | 57 | 97 | NM | 121 | NM | NM | NM | 59 = 33 | 499 = 63 |
| TS (MPa) @ 0 hr | 140 | 141 | 146 | 140 | 144 | 142 | 137 | 120 | NT* |
| TS-1 (MPa) @ 150 hr | 41 | 61 | 90 | 74 | 90 | 95 | 91 | 35 | NT |
| %-age Retained TS-1 | 30 | 43 | 61 | 53 | 63 | 67 | 66 | 29 | NT |
| TS-2 (MPa) @ 100 hr | 46 | 67 | 98 | 80 | 101 | 103 | 101 | 34 | NT |
| %-age Retained TS-2 | 33 | 47 | 67 | 57 | 70 | 73 | 74 | 28 | NT |

*NT—not tested due to high viscosity

TABLE 13

| | C64 | C65 | C66 | C67 | C68 | C69 | C70 | C71 | C72 | C73 |
|---|---|---|---|---|---|---|---|---|---|---|
| MATERIAL | | | | | | | | | | |
| Glass Fiber B | 30 | 30 | 30 | 30 | 30 | 30 | 30 | 30 | 30 | 30 |
| PBT | 47.55 | 47.05 | 46.05 | 45.05 | 46.05 | 45.05 | 44.05 | 45.05 | 44.05 | 43.05 |
| Antioxidant | 0.15 | 0.15 | 0.15 | 0.15 | 0.15 | 0.15 | 0.15 | 0.15 | 0.15 | 0.15 |
| PTFE | 0.25 | 0.25 | 0.25 | 0.25 | 0.25 | 0.25 | 0.25 | 0.25 | 0.25 | 0.25 |
| SAN | 0.25 | 0.25 | 0.25 | 0.25 | 0.25 | 0.25 | 0.25 | 0.25 | 0.25 | 0.25 |
| FR Synergist | 8.5 | 8.5 | 8.5 | 8.5 | 8.5 | 8.5 | 8.5 | 8.5 | 8.5 | 8.5 |
| Flame Retardant | 13.3 | 13.3 | 13.3 | 13.3 | 13.3 | 13.3 | 13.3 | 13.3 | 13.3 | 13.3 |
| MF Epoxy C | 0 | 0.5 | 1.5 | 2.5 | 0.5 | 1.5 | 2.5 | 0.5 | 1.5 | 2.5 |
| $Ca_5(PO_4)_3OH$ | 0 | 0 | 0 | 0 | 1 | 1 | 1 | 2 | 2 | 2 |
| PHYSICAL PROPERTY | | | | | | | | | | |
| CE, meq/kg PBT | 0 | 45 | 139 | 236 | 46 | 142 | 242 | 47 | 145 | 247 |
| MV-5 | 115 | 118 | 145 | 189 | 180 | 148 | 112 | 126 | 156 | 162 |
| MV-10 = %-age MV-5 | 107 = 92 | 119 = 99 | 204 = 141 | 387 = 205 | 446 = 248 | 235 = 159 | 109 = 97 | 149 = 118 | 295 = 189 | 305 = 188 |
| MV-16 = %-age MV-5 | 98 = 87 | 118 = 97 | 339 = 234 | 481 = 254 | 549 = 305 | 356 = 241 | 113 = 101 | 192 = 152 | 408 = 262 | 383 = 236 |
| MV-21 = %-age MV-5 | 93/85 | 115 = 93 | 448 = 309 | 548 = 290 | 602 = 334 | 437 = 295 | 107 = 96 | 148 = 117 | 533 = 342 | 412 = 254 |
| MV-26 = %-age MV-5 | 91/79 | 111 = 86 | 478 = 330 | 606 = 321 | 591 = 328 | 417 = 282 | 101 = 90 | 197 = 156 | 491 = 315 | 403 = 249 |

TABLE 13-continued

|  | C64 | C65 | C66 | C67 | C68 | C69 | C70 | C71 | C72 | C73 |
|---|---|---|---|---|---|---|---|---|---|---|
| MV-32 = %-age MV-5 | 85/78 | 102 = 90 | 442 = 305 | 553 = 293 | 568 = 316 | 384 = 259 | 94 = 84 | 156 = 124 | 427 = 274 | 382 = 236 |
| MV-39 = %-age MV-5 | 83/76 | 107 = 84 | 405 = 279 | NM | NM | 351 = 237 | 94 = 84 | 187 = 148 | 401 = 257 | 358 = 221 |
| MV-43 = %-age MV-5 | 81/74 | 100 = 82 | 388 = 268 | NM | NM | 333 = 225 | 90 = 80 | 190 = 151 | 366 = 235 | 329 = 203 |
| MV-48 = %-age MV-5 | 79/68 | 97 = 82 | 371 = 256 | NM | NM | 325 = 220 | 82 = 73 | 126 = 100 | 355 = 228 | NM |
| MV-53 = %-age MV-5 | 73/63 | 98 = 78 | 363 = 250 | NM | NM | 316 = 214 | 80 = 71 | NM | 346 = 222 | NM |
| MV-59 = %-age MV-5 | 67/56 | 93 = 71 | 349 = 241 | NM | NM | 289 = 195 | 78 = 70 | NM | 323 = 207 | NM |
| MV-63 = %-age MV-5 | 60 | 84 | 323 = 223 | NM | NM | 257 = 174 | 71 | NM | 266 = 171 | NM |
| TS (MPa) @ 0 hr | 95 | 93 | 91 | 90 | 87 | 83 | 90 | 89 | 87 | 87 |
| TS-1 (MPa) @ 150 hr | 6.8 | 6.5 | 7.3 | 8.9 | 6 | 2.8 | 2 | 1.7 | 4.9 | 2.6 |
| %-age TS-1 retained | 7 | 7 | 8 | 10 | 7 | 3 | 2 | 2 | 6 | 3 |

TABLE 14

|  | C74 | C75 | E18 | E19 | C76 | C77 | C78 | C79 |
|---|---|---|---|---|---|---|---|---|
| MATERIAL |  |  |  |  |  |  |  |  |
| Glass Fiber A | 15 | 15 | 15 | 15 | 15 | 15 | 15 | 15 |
| PBT | 84.2 | 75.9 | 74.9 | 73.9 | 74.2 | 65.9 | 64.9 | 63.9 |
| Antioxidant | 0.3 | 0.3 | 0.3 | 0.3 | 0.3 | 0.3 | 0.3 | 0.3 |
| Lubricant | 0.5 | 0.5 | 0.5 | 0.5 | 0.5 | 0.5 | 0.5 | 0.5 |
| Toughener | 0 | 6 | 6 | 6 | 0 | 6 | 6 | 6 |
| MF Epoxy A | 0 | 1.9 | 1.9 | 1.9 | 0 | 1.9 | 1.9 | 1.9 |
| MF Epoxy B | 0 | 0.4 | 0.4 | 0.4 | 0 | 0.4 | 0.4 | 0.4 |
| $Ca_5(PO_4)_3OH$ | 0 | 0 | 1 | 2 | 0 | 0 | 1 | 2 |
| Flame Retardant | 0 | 0 | 0 | 0 | 10 | 10 | 10 | 10 |
| PHYSICAL PROPERTY |  |  |  |  |  |  |  |  |
| CE, meq/kg PBT | 0 | 92 | 93 | 94 | 0 | 106 | 107 | 109 |
| MV-5 | 115 | 101 | 115 | 120 | 85 | 85 | 84 | 101 |
| MV-10 = %-ageMV-5 | 90 = 78 | 81 = 80 | 96 = 83 | 102 = 85 | 74 = 87 | 81 = 95 | 78 = 93 | 92 = 91 |
| MV-16 = %-age MV-5 | 79 = 69 | 79 = 78 | 83 = 72 | 89 = 74 | 63 = 74 | 90 = 106 | 76 = 90 | 86 = 85 |
| MV-21 = %-age MV-5 | 70 = 61 | 89/88 | 7162 | 81 = 68 | 55 = 65 | 98/115 | 79/94 | 84 = 83 |
| MV-26 = %-age MV-5 | 62 = 54 | 133 = 132 | 66 = 57 | 77 = 64 | 49 = 58 | 103 = 121 | 79 = 94 | 83 = 82 |
| MV-32 = %-age MV-5 | 56 = 49 | 257 = 254 | 72 = 63 | 76 = 63 | 43 = 51 | 109 = 128 | 83 = 99 | 84 = 83 |
| MV-39 = %-age MV-5 | 51 = 44 | 327 = 324 | 76 = 66 | 74 = 62 | 41 = 48 | 114 = 134 | 77 = 92 | 76 = 75 |
| MV-43 = %-age MV-5 | 47 = 41 | 441 = 437 | 84 = 73 | 80 = 67 | 38 = 45 | 120 = 141 | 84 = 100 | 78 = 77 |
| MV-48 = %-age MV-5 | 43 = 37 | 538 = 533 | 88 = 77 | 83 = 69 | 33 = 39 | 139 = 164 | 85 = 101 | 74 = 73 |
| MV-53 = %-age MV-5 | 39 = 34 | 570 = 564 | 94 = 82 | 81 = 68 | 30 = 35 | 144 = 169 | 88 = 105 | 70 = 69 |
| MV-59 = %-age MV-5 | 37 = 32 | 589 = 583 | 98 = 85 | 80 = 67 | 30 = 35 | 179 = 211 | 84 = 100 | 72 = 71 |
| MV-63 = %-age MV-5 | 33 | 622 | 103 | 87 | 28 | 194 | 85 | 69 |
| TS (MPa) @ 0 hr | 108 | 105 | 98 | 97 | 73 | 68 | 69 | 72 |
| TS-1 (MPa) @ 150 hr | 24 | 81 | 74 | 74 | 5 | 5 | 5 | 5 |
| %-age Retained TS-1 | 23 | 77 | 76 | 76 | 6 | 7 | 8 | 7 |

TABLE 15

|  | C80 | C81 | C82 | E20 | E21 |
|---|---|---|---|---|---|
| MATERIAL |  |  |  |  |  |
| Glass Fiber B | 30 | 30 | 30 | 30 | 30 |
| PET | 66.13 | 59.13 | 58.13 | 56.63 | 55.13 |
| Antioxidant | 0.1 | 0.1 | 0.1 | 0.1 | 0.1 |
| Lubricant | 0.5 | 0.5 | 0.5 | 0.5 | 0.5 |
| Toughener | 0 | 4.0 | 4.0 | 4.0 | 4.0 |
| MF Epoxy A | 0 | 3.0 | 4.0 | 4.0 | 4.0 |
| $Ca_5(PO_4)_3OH$ | 0 | 0 | 0 | 1.5 | 3.0 |
| Plasticizer | 2.77 | 2.77 | 2.77 | 2.77 | 2.77 |
| Talc | 0.5 | 0.5 | 0.5 | 0.5 | 0.5 |
| PHYSICAL PROPERTY |  |  |  |  |  |
| CE, meq/kg PET | 0 | 102 | 131 | 134 | 138 |
| MV-5 | 66 | 95 | 106 | 143 | 123 |
| MV-10 = %-age MV-5 | 53 = 80 | 98 = 103 | 101 = 95 | 144 = 101 | 124 = 101 |
| MV-16 = %-age MV-5 | 47 = 71 | 100 = 105 | 124 = 117 | 138 = 97 | 116 = 97 |
| MV-21 = %-age MV-5 | 43 = 65 | 10 = 111 | 157 = 148 | 133 = 93 | 102 = 83 |
| MV-26 = %-age MV-5 | 37 = 56 | 123 = 129 | 269 = 254 | 129 = 90 | 97 = 79 |
| MV-32 = %-age MV-5 | 36 = 55 | 143 = 151 | 418 = 394 | 124 = 87 | 95 = 77 |

TABLE 15-continued

|  | C80 | C81 | C82 | E20 | E21 |
|---|---|---|---|---|---|
| MV-39 = %-age MV-5 | 34 = 52 | 171 = 180 | 509 = 480 | 121 = 85 | 88 = 72 |
| MV-43 = %-age MV-5 | 31 = 47 | 194 = 204 | 544 = 513 | 121 = 85 | 85 = 69 |
| MV-48 = %-age MV-5 | 33 = 50 | 226 = 238 | 569 = 537 | 118 = 83 | 89 = 72 |
| MV-53 = %-age MV-5 | 30 = 45 | 252 = 265 | 562 = 530 | 114 = 80 | 75 = 61 |
| MV-59 = %-age MV-5 | NM | 258 = 272 | 556 = 525 | 108 = 76 | 80 = 65 |
| MV-63 = %-age MV-5 | NM | 253 = 266 | 526 = 496 | 103 = 72 | 75 = 61 |
| TS (MPa) @ 0 hr | 158 | 147 | 146 | 152 | 143 |
| TS-1 (MPa) @ 75 hr | 53 | 98 | 108 | 111 | 91 |
| %-age Retained TS-1 | 33 | 67 | 74 | 73 | 63 |
| TS-2 (MPa) @ 25 hr | 76 | 119 | 123 | 128 | 114 |
| %-age Retained TS-2 | 48 | 81 | 84 | 84 | 80 |

The invention claimed is:

1. A composition comprising:
a) 40 to 89 weight percent of at least one semi-aromatic polyester resin selected from the group consisting of polyethylene terephthalate, poly(trimethylene terephthalate), and polybutylene terephthalate, polyethylene naphthalene, and combinations of these;
b) 10 to 50 weight percent of at least one reinforcing agent;
c) 0.5 to 5.0 weight percent hydroxyapatite;
d) 0.5 to 4.0 weight percent of at least one epoxy component having two or more epoxy functional groups per molecule of the epoxy component;
e) optionally, 0.5 to 15 weight percent of at least one toughener,
(d) and (e) having a combined epoxy functionality ranging from 40 and 500 milliequivalents per kilogram of the semi-aromatic polyester resin; and
wherein:
when measured according to Test (A), each subsequent melt viscosity of the polyester composition is not greater than 160% of its initial melt viscosity and
when measured according to Test (B), the tensile strength of exposed test bars comprising the polyester composition is at least 60% of that of unexposed bars comprising the same polyester composition;
whereby:
Test (A) comprises:
measuring initial melt viscosity of the polyester composition at five minutes after heating the polyester composition at a temperature between 30 and 45° C. above the melting point of the semi-aromatic polyester, and
measuring subsequent melt viscosities of the polyester composition at intervals between greater than 5 minutes and 48 minutes, including measurements at 21 and 48 minutes, while the temperature of the polyester composition is maintained between 30 and 45° C. above the melting point of the semi-aromatic polyester,
wherein the measuring is done according to ISO 11443 at 1000 sec$^{-1}$;
and
Test (B) comprises:
measuring tensile strength of unexposed test bars comprising the polyester composition;
exposing test bars comprising the same polyester composition for a duration of at least 25 hours to steam at 100 percent relative humidity, pressure of 2 atmospheres, and temperature of 121° C.; and
measuring at the end of the duration tensile strength of the exposed test bars, wherein the measuring is done according to ISO527-1 and all test bars have been molded according to ISO527-2/1A.

2. The polyester composition of claim 1, wherein when the semi-aromatic polyester resin is polyethylene terephthalate or polybutylene terephthalate:
the quotient of milliequivalents of epoxy functionality per kilogram of semi-aromatic polyester resin over milliequivalents of acid end groups per kilogram of semi-aromatic polyester resin ranges from 2.5 to 10; and
the product of milliequivalents of acid end groups per kilogram of semi-aromatic polyester resin times milliequivalents of epoxy functionality per kilogram of semi-aromatic polyester resin ranges from 1000 to 5000; and
when the semi-aromatic polyester is poly(trimethylene terephthalate):
the quotient of milliequivalents of epoxy functionality per kilogram of semi-aromatic polyester resin over milliequivalents of acid end groups per kilogram of semi-aromatic polyester resin ranges from 2.5 to 15; and
the product of milliequivalents of acid end groups per kilogram of semi-aromatic polyester resin times milliequivalents of epoxy functionality per kilogram of semi-aromatic polyester resin ranges from 200 to 3000.

3. The polyester composition of claim 2, wherein (b) is selected from the group consisting of glass fibers, glass beads, glass flake, mica, and combinations of these.

4. The polyester composition of claim 2, wherein (d) is selected from the group consisting of diphenolic epoxy condensation polymers, condensation products of glycidyl ethers and phenolic polymers, diglycidyl ether of bisphenol A polymers, tetraglycidyl ether of tetra(parahydroxyphenyl) ethane, and combinations of these.

5. The polyester composition of claim 2, wherein (e) is selected from the group of copolymers of $C_1$ to $C_{10}$ alkyl acrylates, ethylene, and glycidyl methacrylate; and combinations of these.

6. The polyester composition of claim 2, wherein the exposure duration is selected from the group consisting of: 100 hours when the semi-aromatic polyester resin is poly (butylene terephthalate), 50 hours when the semi-aromatic polyester resin is poly(trimethylene terephthalate), and 25 hours when the semi-aromatic polyester resin is poly(ethylene terephthalate).

7. The polyester composition of claim 6, having up to 10 weight percent of (e) and wherein:
(d) is selected from the group consisting of diphenolic epoxy condensation polymers, condensation products of glycidyl ethers and phenolic polymers, diglycidyl ether of bisphenol A polymers, tetraglycidyl ether of tetra(parahydroxyphenyl) ethane, and combinations of these; and (e) is selected from the group of copolymers of $C_1$ to $C_{10}$ alkyl acrylates, ethylene, and glycidyl methacrylate; and combinations of these.

8. The polyester composition of claim 1, wherein (b) is selected from the group consisting of glass fibers, glass beads, glass flake, mica, and combinations of these.

9. The polyester composition of claim 1, wherein (d) is selected from the group consisting of diphenolic epoxy condensation polymers, condensation products of glycidyl ethers and phenolic polymers, diglycidyl ether of bisphenol A polymers, tetraglycidyl ether of tetra(parahydroxyphenyl) ethane, and combinations of these.

10. The polyester composition of claim 1, having up to 10 weight percent of (e).

11. The polyester composition of claim 1, wherein (e) is selected from the group of copolymers of $C_1$ to $C_{10}$ alkyl acrylates, ethylene, and glycidyl methacrylate; and combinations of these.

12. The polyester composition of claim 1, wherein the exposure duration is selected from the group consisting of: 100 hours when the semi-aromatic polyester resin is poly(butylene terephthalate), 50 hours when the semi-aromatic polyester resin is poly(trimethylene terephthalate), and 25 hours when the semi-aromatic polyester resin is poly(ethylene terephthalate).

13. An article comprising the polyester composition of claim 1.

14. The article of claim 13, having up to 10 weight percent of (e) and wherein:
(d) is selected from the group consisting of diphenolic epoxy condensation polymers, condensation products of glycidyl ethers and phenolic polymers, diglycidyl ether of bisphenol A polymers, tetraglycidyl ether of tetra(parahydroxyphenyl) ethane, and combinations of these; and
(e) is selected from the group of copolymers of $C_1$ to $C_{10}$ alkyl acrylates, ethylene, and glycidyl methacrylate; and combinations of these.

15. The article of claim 14, in the form of an electronic part, an electrical part, an electrical part in an electric vehicle, an electrical part in a hybrid vehicle, a connector, a plug, a sensor, a relay, a solenoid, or a switch.

16. The article of claim 13, wherein a test plate comprising the same polyester composition as the article has a Comparative Tracking Index of at least 400.

17. A method of making, comprising:
melt-mixing, to form a polyester composition:
a) 40 to 89 weight percent of at least one semi-aromatic polyester resin selected from the group consisting of polyethylene terephthalate, poly(trimethylene terephthalate), and polybutylene terephthalate, polyethylene naphthalene, and combinations of these;
b) 10 to 50 weight percent of at least one reinforcing agent;
c) 0.5 to 5.0 weight percent hydroxyapatite;
d) 0.5 to 4.0 weight percent of at least one epoxy compound having two or more epoxy functional groups per molecule;
e) optionally, 0.5 to 15 weight percent of at least one toughener,
(d) and (e) having a combined epoxy functionality ranging from 40 and 500 milliequivalents per kilogram of the semi-aromatic polyester resin; and
wherein:
when measured according to Test (A), each subsequent melt viscosity of the polyester composition is not greater than 160% of its initial melt viscosity and when measured according to Test (B), the tensile strength of exposed test bars comprising the polyester composition is at least 60% of that of unexposed bars comprising the same polyester composition;
whereby:
Test (A) comprises:
measuring initial melt viscosity of the polyester composition at five minutes after heating the polyester composition at a temperature between 30 and 45° C. above the melting point of the semi-aromatic polyester resin, and
measuring subsequent melt viscosities of the polyester composition at intervals between greater than 5 minutes and 48 minutes, including measurements at 21 and 48 minutes, while the temperature of the polyester composition is maintained between 30 and 45° C. above the melting point of the semi-aromatic polyester,
wherein the measuring is done according to ISO 11443 at 1000 sec$^{-1}$; and
Test (B) comprises:
measuring tensile strength of unexposed test bars comprising the polyester composition;
exposing test bars comprising the same polyester composition for a duration of at least 25 hours to steam at 100 percent relative humidity, pressure of 2 atmospheres, and temperature of 121° C.; and
measuring at the end of the duration tensile strength of the exposed test bars, wherein the measuring is done according to ISO527-1 and all test bars have been molded according to ISO527-2/1A.

18. The method of claim 17, wherein:
when the semi-aromatic polyester resin is polyethylene terephthalate or polybutylene terephthalate:
the quotient of milliequivalents of epoxy functionality per kilogram of semi-aromatic polyester resin over milliequivalents of acid end groups per kilogram of semi-aromatic polyester resin ranges from 2.5 to 10; and
the product of milliequivalents of acid end groups per kilogram of semi-aromatic polyester resin times milliequivalents of epoxy functionality per kilogram of semi-aromatic polyester resin ranges from 1000 to 5000; and
when the semi-aromatic polyester is poly(trimethylene terephthalate):
the quotient of milliequivalents of epoxy functionality per kilogram of semi-aromatic polyester resin over milliequivalents of acid end groups per kilogram of semi-aromatic polyester resin ranges from 2.5 to 15; and
the product of milliequivalents of acid end groups per kilogram of semi-aromatic polyester resin times milliequivalents of epoxy functionality per kilogram of semi-aromatic polyester resin ranges from 200 to 3000.

19. The method of claim 18, wherein:
the semi-aromatic polyester composition has up to 10 weight percent of (e);
(d) is selected from the group consisting of diphenolic epoxy condensation polymers, condensation products of glycidyl ethers and phenolic polymers, diglycidyl ether of bisphenol A polymers, tetraglycidyl ether of tetra(parahydroxyphenyl) ethane, and combinations of these; and
(e) is selected from the group of copolymers of $C_1$ to $C_{10}$ alkyl acrylates, ethylene, and glycidyl methacrylate; and combinations of these.

20. A composition comprising:
a) 40 to 89 weight percent of at least one semi-aromatic polyester resin selected from the group consisting of polyethylene terephthalate, poly(trimethylene terephthalate), and polybutylene terephthalate, polyethylene naphthalene, and combinations of these;
b) 10 to 50 weight percent of at least one reinforcing agent;
c) 0.5 to 5.0 weight percent hydroxyapatite;
d) 0.5 to 4.0 weight percent of at least one epoxy component having two or more epoxy functional groups per molecule of the epoxy component;
e) optionally, 0.5 to 15 weight percent of at least one toughener, (d) and (e) having a combined epoxy functionality ranging from 40 and 500 milliequivalents per kilogram of the semi-aromatic polyester resin; and
wherein:
when measured according to Test (A), each subsequent melt viscosity of the polyester composition is not greater than 160% of its initial melt viscosity and
when measured according to Test (B), the tensile strength of exposed test bars comprising the polyester composition is at least 60% of that of unexposed bars comprising the same polyester composition;
said composition does not comprise compounds exhibiting a pH of 8 or greater or 6 or less, said pH measured by adding about 100 g/L of the compound to deionized water at 20° C.;

whereby:
Test (A) comprises:
measuring initial melt viscosity of the polyester composition at five minutes after heating the polyester composition at a temperature between 30 and 45° C. above the melting point of the semi-aromatic polyester, and
measuring subsequent melt viscosities of the polyester composition at intervals between greater than 5 minutes and 48 minutes, including measurements at 21 and 48 minutes, while the temperature of the polyester composition is maintained between 30 and 45° C. above the melting point of the semi-aromatic polyester,
wherein the measuring is done according to ISO 11443 at 1000 sec$^{-1}$;
and
Test (B) comprises:
measuring tensile strength of unexposed test bars comprising the polyester composition;
exposing test bars comprising the same polyester composition for a duration of at least 25 hours to steam at 100 percent relative humidity, pressure of 2 atmospheres, and temperature of 121° C.; and
measuring at the end of the duration tensile strength of the exposed test bars, wherein the measuring is done according to ISO527-1 and all test bars have been molded according to ISO527-2/1A.

* * * * *